United States Patent
Tschopp et al.

(10) Patent No.: US 7,385,032 B2
(45) Date of Patent: Jun. 10, 2008

(54) BIMER OR AN OLIGOMER OF A DIMER, TRIMER, QUADROMER OR PENTAMER OF RECOMBINANT FUSION PROTEINS

(75) Inventors: Jürg Tschopp, Epalinges (CH); Pascal Schneider, Epalinges (CH); Nils Holler, Radelfingen (CH)

(73) Assignee: Apotech Research and Development Ltd. (CH)

( * ) Notice: Subject to any disclaimer, the term of this patent is extended or adjusted under 35 U.S.C. 154(b) by 962 days.

(21) Appl. No.: 10/185,425

(22) Filed: Jun. 28, 2002

(65) Prior Publication Data

US 2003/0053984 A1 Mar. 20, 2003

Related U.S. Application Data

(63) Continuation of application No. PCT/EP00/13032, filed on Dec. 20, 2000.

(30) Foreign Application Priority Data

Dec. 30, 1999 (DE) ................................. 199 63 859

(51) Int. Cl.
C07K 14/00 (2006.01)
C07K 14/47 (2006.01)
C07K 14/435 (2006.01)
C07H 21/04 (2006.01)

(52) U.S. Cl. ....................... 530/350; 530/300; 536/23.4
(58) Field of Classification Search ...................... None
See application file for complete search history.

(56) References Cited

U.S. PATENT DOCUMENTS

| 5,763,733 A | 6/1998 | Whitlow et al. ........... 530/387.3 |
| 5,869,330 A * | 2/1999 | Scherer et al. ............. 435/320.1 |
| 6,617,135 B1 * | 9/2003 | Gillies et al. ............... 435/69.7 |
| 2005/0158831 A1 * | 7/2005 | Kornbluth ................... 435/69.5 |

FOREIGN PATENT DOCUMENTS

| WO | WO-97/33617 | 9/1997 |
| WO | WO-99/02711 | 1/1999 |
| WO | WO-99/04000 | 1/1999 |
| WO | WO-99/42597 | 8/1999 |
| WO | WO-00/73444 | 12/2000 |

OTHER PUBLICATIONS

Kishore et al. Biochem J. (1988), vol. 333, pp. 27-32.*
Skolnick et al. From genes protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Suda et al. Molecular cloning and expression of the Fas ligand, a novel member of the tumor necrosis factor family. Cell 75: 1169-1178, 1993.*
Alderson, M..,"Fas ligand mediates activation-induced cell death in human T lymphocytes", *Database Swall Online!—Swall:FASL Human; AC*: P48023, Feb. 1, 1996, XP002167591, 2 pages.
Kishore, Uday.,et al.,"Functional characterization of a recombinant form of the C-terminal, globular head region of the B-chain of human serum complement protein, C1q", *Biochem.J.*, vol. 333,(Mar. 1998),27-32.
Scherer, Philipp E., et al., "A novel serum protein similar to C1q, produced exclusively in adipocytes", *The Journal of Biological Chemistry*, vol. 270, No. 45 (Nov. 10, 1995), 26746-26749 (XP000612012).
Schneider, Pascal.,et al. ,"Conversion of membrane-bound Fas (CD95) ligand to its soluble form is associated with downregulation of its proapoptotic activity and loss of liver toxicity", *J. Exp. Med*, vol. 187, No. 8,(Apr. 20, 1998),1205-1213.
Terskikh, Alexy.V. ,et al., ""Peptabody": A new type of high avidity binding protein", *Proc. Natl. Ada. Sci.* USA, vol. 94,(Mar. 1997),1663-1668.

* cited by examiner

*Primary Examiner*—Bridget E Bunner
(74) *Attorney, Agent, or Firm*—Connolly Bove Lodge & Hutz LLP

(57) ABSTRACT

The invention relates to oligomers of a dimer, trimer, quatromer or pentamer of recombinant fusion proteins. The oligomers are characterized in that the recombinant fusion proteins have at least one component A and at least one component B, whereby component A contains a protein or a protein segment with a biological function, in particular with a ligand function for antibodies, for soluble or membranous signal molecules, for receptors or an antibody, or an antibody segment, and component B contains a protein or a protein segment which dimerizes or oligomerizes the dimer, trimer, quatromer or pentamer of the recombinant fusion protein, without the action of third-party molecules. The invention also relates to the use of dimers or oligomers of this type for producing a medicament, to the fusion proteins which cluster in dimers or oligomers and to their DNA sequence and expression vectors or host cells comprising this DNA sequence.

12 Claims, 20 Drawing Sheets

Figure 1:
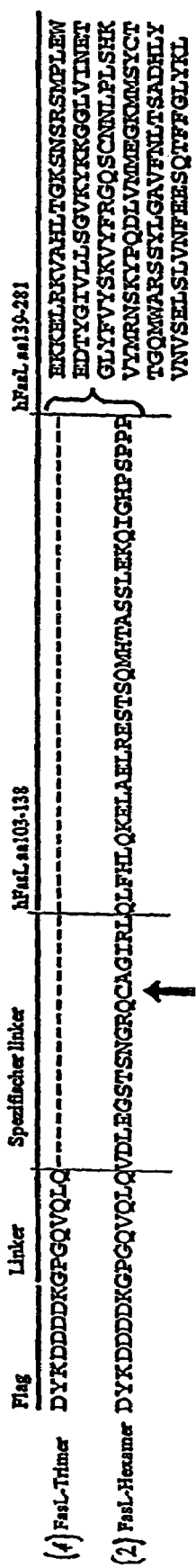

A nr  Non-reducing conditions r   Reducing conditions

B

|   | Flag | Linker | mACRP30 aa 18-111 | hFasL aa 139-281 |
|---|---|---|---|---|

(4) FasL-ACRP30 DYKDDDDKGPGQVQLH EDDVTTTEELAPALVPPKGTCAGWMAGIPGHPGHNGTPGRDG TPGEKGEKGDAGLLQPKGETGDVGMTGAEGPRGFPGTPGRKGEPGE LQ EKKELRKVAHLTGKSNSRSMPLEWEDTYGI
LLSGVKYKKGGLVINETGLYFVYSKVYFR
GQSCNNLPLSHKVYMRNSKYPQDLVMMEG
KMSYCTTGQMWARSSYLGAVFNLTSADH
LYVNVSELSLVNFEESQTFFGLYKL

```
                    Linker
```

Fig. 6

(7) CD40L-ACRP30 DYKDDDDKGPGPGQVQLH EDDVTTEELAPALVPPKGTCAGWMAGIPGHPGHNGTPGRDGRDG LQGDQNPQIAAHVISEASSKTTSVLQWAEKGY
TPGEKGEKGDAGLLGPKGETGDVGMTGAEGPRGFPGTPGRKGEPGE TMSNNLVTLENGKQLTVKRQGLYYIYAQV
TFCSNREASSQAPFIASLCLKSPGRFERI
LLRAANTHSSAKPCGQQSIHLGGVFELQP
GASVFVNVTDPSQVSHGTGFTSFGLLKL

Flag — Linker — mACRP30 aa 18-111 — Linker — hCD40L aa116-261

Fig.12

SEQUENCE LISTING

<160> NUMBER OF SEQ ID NOS: 24

<210> SEQ ID NO 1
<211> LENGTH: 159
<212> TYPE: PRT
<213> ORGANISM: Artificial Sequence
<220> FEATURE:
<223> OTHER INFORMATION: FasL-Trimer
<220> FEATURE:
<221> NAME/KEY: DOMAIN
<222> LOCATION: (9)...(16)
<223> OTHER INFORMATION: Sequence at C-terminus of oligomerization
      domain
<220> FEATURE:
<221> NAME/KEY: DOMAIN
<222> LOCATION: (17)...(159)
<223> OTHER INFORMATION: Linker
<223> OTHER INFORMATION: humanFasL aa 139-281
<220> FEATURE:
<223> OTHER INFORMATION: Sequence at C-terminus of oligomerization
      domain

<400> SEQUENCE: 1

Asp Tyr Lys Asp Asp Asp Asp Lys Gly Pro Gly Gln Val Gln Leu Gln
 1               5                  10                  15

Glu Lys Lys Glu Leu Arg Lys Val Ala His Leu Thr Gly Lys Ser Asn
            20                  25                  30

Ser Arg Ser Met Pro Leu Glu Trp Glu Asp Thr Tyr Gly Ile Val Leu
        35                  40                  45

Leu Ser Gly Val Lys Tyr Lys Lys Gly Gly Leu Val Ile Asn Glu Thr
    50                  55                  60

Gly Leu Tyr Phe Val Tyr Ser Lys Val Tyr Phe Arg Gly Gln Ser Cys
65                  70                  75                  80

Asn Asn Leu Pro Leu Ser His Lys Val Tyr Met Arg Asn Ser Lys Tyr
                85                  90                  95

Pro Gln Asp Leu Val Met Met Glu Gly Lys Met Met Ser Tyr Cys Thr
                100                 105                 110

Thr Gly Gln Met Trp Ala Arg Ser Ser Tyr Leu Gly Ala Val Phe Asn
            115                 120                 125

Leu Thr Ser Ala Asp His Leu Tyr Val Asn Val Ser Glu Leu Ser Leu
130                 135                 140

Val Asn Phe Glu Glu Ser Gln Thr Phe Phe Gly Leu Tyr Lys Leu
145                 150                 155

<210> SEQ ID NO 2
<211> LENGTH: 213
<212> TYPE: PRT
<213> ORGANISM: Artificial Sequence
<220> FEATURE:
<223> OTHER INFORMATION: FasL-Hexamer
<220> FEATURE:
<221> NAME/KEY: DOMAIN
<222> LOCATION: (1)...(8)
<223> OTHER INFORMATION: Flag
<220> FEATURE:
<221> NAME/KEY: DOMAIN
<222> LOCATION: (9)...(16)
<223> OTHER INFORMATION: Linker
<220> FEATURE:
<221> NAME/KEY: DOMAIN
<222> LOCATION: (17)...(34)
<223> OTHER INFORMATION: Specific Linker
<220> FEATURE:
<221> NAME/KEY: DOMAIN
<222> LOCATION: (35)...(70)
<223> OTHER INFORMATION: humanFasL aa 103-138
<220> FEATURE:
<221> NAME/KEY: DOMAIN
<222> LOCATION: (71)...(213)
<223> OTHER INFORMATION: humanFasL aa 139-281

<400> SEQUENCE: 2

Asp Tyr Lys Asp Asp Asp Asp Lys Gly Pro Gly Gln Val Gln Leu Gln
1               5                   10                  15

Val Asp Leu Glu Gly Ser Thr Ser Asn Gly Arg Gln Cys Ala Gly Ile
            20                  25                  30

Arg Leu Gln Leu Phe His Leu Gln Lys Glu Leu Ala Glu Leu Arg Glu
        35                  40                  45

Ser Thr Ser Gln Met His Thr Ala Ser Ser Leu Glu Lys Gln Ile Gly
    50                  55                  60

His Pro Ser Pro Pro Pro Glu Lys Lys Glu Leu Arg Lys Val Ala His
65                  70                  75                  80

Leu Thr Gly Lys Ser Asn Ser Arg Ser Met Pro Leu Glu Trp Glu Asp
                85                  90                  95

Thr Tyr Gly Ile Val Leu Leu Ser Gly Val Lys Tyr Lys Lys Gly Gly
                100                 105                 110

Leu Val Ile Asn Glu Thr Gly Leu Tyr Phe Val Tyr Ser Lys Val Tyr
            115                 120                 125

Phe Arg Gly Gln Ser Cys Asn Asn Leu Pro Leu Ser His Lys Val Tyr

-continued

```
            130                 135                 140
Met Arg Asn Ser Lys Tyr Pro Gln Asp Leu Val Met Met Glu Gly Lys
145                 150                 155                 160

Met Met Ser Tyr Cys Thr Thr Gly Gln Met Trp Ala Arg Ser Ser Tyr
                165                 170                 175

Leu Gly Ala Val Phe Asn Leu Thr Ser Ala Asp His Leu Tyr Val Asn
                180                 185                 190

Val Ser Glu Leu Ser Leu Val Asn Phe Glu Glu Ser Gln Thr Phe Phe
            195                 200                 205

Gly Leu Tyr Lys Leu
        210

<210> SEQ ID NO 3
<211> LENGTH: 213
<212> TYPE: PRT
<213> ORGANISM: Artificial Sequence
<220> FEATURE:
<223> OTHER INFORMATION: Super-FasL
<220> FEATURE:
<221> NAME/KEY: DOMAIN
<222> LOCATION: (1)...(8)
<223> OTHER INFORMATION: Flag
<220> FEATURE:
<221> NAME/KEY: DOMAIN
<222> LOCATION: (9)...(16)
<223> OTHER INFORMATION: Linker
<220> FEATURE:
<221> NAME/KEY: DOMAIN
<222> LOCATION: (17)...(34)
<223> OTHER INFORMATION: Specific Linker
<220> FEATURE:
<221> NAME/KEY: DOMAIN
<222> LOCATION: (35)...(70)
<223> OTHER INFORMATION: humanFasL aa 103-138
<220> FEATURE:
<221> NAME/KEY: DOMAIN
<222> LOCATION: (71)...(213)
<223> OTHER INFORMATION: humanFasL aa 139-281

<400> SEQUENCE: 3

Asp Tyr Lys Asp Asp Asp Asp Lys Gly Pro Gly Gln Val Gln Leu Gln
1               5                   10                  15

Val Asp Leu Glu Gly Ser Thr Ser Asn Gly Arg Gln Ser Ala Gly Ile
            20                  25                  30

Arg Leu Gln Leu Phe His Leu Gln Lys Glu Leu Ala Glu Leu Arg Glu
        35                  40                  45

Ser Thr Ser Gln Met His Thr Ala Ser Ser Leu Glu Lys Gln Ile Gly
    50                  55                  60

His Pro Ser Pro Pro Pro Glu Lys Lys Glu Leu Arg Lys Val Ala His
65                  70                  75                  80

Leu Thr Gly Lys Ser Asn Ser Arg Ser Met Pro Leu Glu Trp Glu Asp
                85                  90                  95

Thr Tyr Gly Ile Val Leu Leu Ser Gly Val Lys Tyr Lys Lys Gly Gly
            100                 105                 110

Leu Val Ile Asn Glu Thr Gly Leu Tyr Phe Val Tyr Ser Lys Val Tyr
        115                 120                 125

Phe Arg Gly Gln Ser Cys Asn Asn Leu Pro Leu Ser His Lys Val Tyr
    130                 135                 140

Met Arg Asn Ser Lys Tyr Pro Gln Asp Leu Val Met Met Glu Gly Lys
145                 150                 155                 160

Met Met Ser Tyr Cys Thr Thr Gly Gln Met Trp Ala Arg Ser Ser Tyr
                165                 170                 175
```

```
Leu Gly Ala Val Phe Asn Leu Thr Ser Ala Asp His Leu Tyr Val Asn
            180                 185                 190

Val Ser Glu Leu Ser Leu Val Asn Phe Glu Glu Ser Gln Thr Phe Phe
        195                 200                 205

Gly Leu Tyr Lys Leu
        210

<210> SEQ ID NO 4
<211> LENGTH: 252
<212> TYPE: PRT
<213> ORGANISM: Artificial Sequence
<220> FEATURE:
<223> OTHER INFORMATION: FasL-ACRP30
<220> FEATURE:
<221> NAME/KEY: DOMAIN
<222> LOCATION: (1)...(8)
<223> OTHER INFORMATION: Flag
<220> FEATURE:
<221> NAME/KEY: DOMAIN
<222> LOCATION: (9)...(16)
<223> OTHER INFORMATION: Linker
<220> FEATURE:
<221> NAME/KEY: DOMAIN
<222> LOCATION: (17)...(108)
<223> OTHER INFORMATION: mouseACRP30 aa 18-111
<220> FEATURE:
<221> NAME/KEY: DOMAIN
<222> LOCATION: (109)...(110)
<223> OTHER INFORMATION: Linker
<220> FEATURE:
<221> NAME/KEY: DOMAIN
<222> LOCATION: (111)...(252)
<223> OTHER INFORMATION: humanFasL aa 139-281

<400> SEQUENCE: 4

Asp Tyr Lys Asp Asp Asp Asp Lys Gly Pro Gly Gln Val Gln Leu His
  1               5                  10                  15

Glu Asp Asp Val Thr Thr Thr Glu Glu Leu Ala Pro Ala Leu Val Pro
            20                  25                  30

Pro Pro Lys Gly Thr Cys Ala Gly Trp Met Ala Gly Ile Pro Gly His
        35                  40                  45

Pro Gly His Asn Gly Thr Pro Gly Arg Asp Gly Arg Asp Gly Thr Pro
    50                  55                  60

Gly Glu Lys Gly Glu Lys Gly Asp Ala Gly Leu Leu Gly Pro Lys Gly
 65                  70                  75                  80

Glu Thr Gly Asp Val Gly Met Thr Gly Ala Glu Gly Pro Arg Gly Phe
            85                  90                  95

Pro Gly Thr Pro Gly Arg Lys Gly Glu Pro Gly Glu Leu Gln Glu Lys
        100                 105                 110

Lys Glu Leu Arg Lys Val Ala His Leu Thr Gly Lys Ser Asn Ser Arg
    115                 120                 125

Ser Met Pro Leu Glu Trp Glu Asp Thr Tyr Gly Ile Leu Leu Ser Gly
        130                 135                 140

Val Lys Tyr Lys Lys Gly Gly Leu Val Ile Asn Glu Thr Gly Leu Tyr
145                 150                 155                 160

Phe Val Tyr Ser Lys Val Tyr Phe Arg Gly Gln Ser Cys Asn Asn Leu
                165                 170                 175

Pro Leu Ser His Lys Val Tyr Met Arg Asn Ser Lys Tyr Pro Gln Asp
            180                 185                 190

Leu Val Met Met Glu Gly Lys Met Met Ser Tyr Cys Thr Thr Gly Gln
        195                 200                 205
```

```
Met Trp Ala Arg Ser Ser Tyr Leu Gly Ala Val Phe Asn Leu Thr Ser
    210                 215                 220
Ala Asp His Leu Tyr Val Asn Val Ser Glu Leu Ser Leu Val Asn Phe
225                 230                 235                 240
Glu Glu Ser Gln Thr Phe Phe Gly Leu Tyr Lys Leu
                245                 250

<210> SEQ ID NO 5
<211> LENGTH: 296
<212> TYPE: PRT
<213> ORGANISM: Artificial Sequence
<220> FEATURE:
<223> OTHER INFORMATION: TRAIL-ACRP30
<220> FEATURE:
<221> NAME/KEY: DOMAIN
<222> LOCATION: (1)...(8)
<223> OTHER INFORMATION: Flag
<220> FEATURE:
<221> NAME/KEY: DOMAIN
<222> LOCATION: (9)...(16)
<223> OTHER INFORMATION: Linker
<220> FEATURE:
<221> NAME/KEY: DOMAIN
<222> LOCATION: (17)...(108)
<223> OTHER INFORMATION: mouseACRP30 aa 18-111
<220> FEATURE:
<221> NAME/KEY: DOMAIN
<222> LOCATION: (109)...(110)
<223> OTHER INFORMATION: Linker
<220> FEATURE:
<221> NAME/KEY: DOMAIN
<222> LOCATION: (111)...(296)
<223> OTHER INFORMATION: humanTRAIL aa 95-281

<400> SEQUENCE: 5

Asp Tyr Lys Asp Asp Asp Asp Lys Gly Pro Gly Gln Val Gln Leu His
  1               5                  10                  15
Glu Asp Asp Val Thr Thr Thr Glu Glu Leu Ala Pro Ala Leu Val Pro
                 20                  25                  30
Pro Pro Lys Gly Thr Cys Ala Gly Trp Met Ala Gly Ile Pro Gly His
             35                  40                  45
Pro Gly His Asn Gly Thr Pro Gly Arg Asp Gly Arg Asp Gly Thr Pro
         50                  55                  60
Gly Glu Lys Gly Glu Lys Gly Asp Ala Gly Leu Leu Gly Pro Lys Gly
 65                  70                  75                  80
Glu Thr Gly Asp Val Gly Met Thr Gly Ala Glu Gly Pro Arg Gly Phe
                 85                  90                  95
Pro Gly Thr Pro Gly Arg Lys Gly Glu Pro Gly Glu Leu Gln Thr Ser
            100                 105                 110
Glu Glu Thr Ile Ser Thr Val Gln Glu Lys Gln Asn Ile Ser Pro
            115                 120                 125     Pro
Leu Val Arg Glu Arg Gly Pro Gln Arg Val Ala Ala Ile Thr Gly Thr
            130                 135                 140
Arg Gly Arg Ser Asn Thr Leu Ser Ser Pro Asn Ser Lys Asn Glu Lys
145                 150                 155                 160
Ala Leu Gly Arg Lys Ile Asn Ser Trp Glu Ser Ser Arg Ser Gly His
                165                 170                 175
Ser Phe Leu Ser Asn Leu His Leu Arg Asn Gly Glu Leu Val Ile His
                180                 185                 190
Glu Lys Gly Phe Tyr Tyr Ile Tyr Ser Gln Thr Tyr Phe Arg Phe Gln
            195                 200                 205
Glu Glu Ile Lys Glu Asn Thr Lys Asn Asp Lys Gln Met Val Gln Tyr
```

-continued

```
                    210                 215                 220
Ile Tyr Lys Tyr Thr Ser Tyr Pro Asp Pro Ile Leu Leu Met Lys Ser
225                 230                 235                 240

Ala Arg Asn Ser Cys Trp Ser Lys Asp Ala Glu Tyr Gly Leu Tyr Ser
                245                 250                 255

Ile Tyr Gln Gly Gly Ile Phe Glu Leu Lys Glu Asn Asp Arg Ile Phe
            260                 265                 270

Val Ser Val Thr Asn Glu His Leu Ile Asp Met Asp His Glu Ala Ser
        275                 280                 285

Phe Phe Gly Ala Phe Leu Val Gly
    290                 295

<210> SEQ ID NO 6
<211> LENGTH: 268
<212> TYPE: PRT
<213> ORGANISM: Artificial Sequence
<220> FEATURE:
<223> OTHER INFORMATION: TNFa-ACRP30
<220> FEATURE:
<221> NAME/KEY: DOMAIN
<222> LOCATION: (1)...(8)
<223> OTHER INFORMATION: Flag
<220> FEATURE:
<221> NAME/KEY: DOMAIN
<222> LOCATION: (9)...(16)
<223> OTHER INFORMATION: Linker
<220> FEATURE:
<221> NAME/KEY: DOMAIN
<222> LOCATION: (17)...(108)
<223> OTHER INFORMATION: mouseACRP30 aa 18-111
<220> FEATURE:
<221> NAME/KEY: DOMAIN
<222> LOCATION: (109)...(110)
<223> OTHER INFORMATION: Linker
<220> FEATURE:
<221> NAME/KEY: DOMAIN
<222> LOCATION: (111)...(268)
<223> OTHER INFORMATION: mouseTNFa aa 77-235

<400> SEQUENCE: 6

Asp Tyr Lys Asp Asp Asp Asp Lys Gly Pro Gly Gln Val Gln Leu His
1               5                   10                  15

Glu Asp Asp Val Thr Thr Thr Glu Glu Leu Ala Pro Ala Leu Val Pro
            20                  25                  30

Pro Pro Lys Gly Thr Cys Ala Gly Trp Met Ala Gly Ile Pro Gly His
        35                  40                  45

Pro Gly His Asn Gly Thr Pro Gly Arg Asp Gly Arg Asp Gly Thr Pro
    50                  55                  60

Gly Glu Lys Gly Glu Lys Gly Asp Ala Gly Leu Leu Gly Pro Lys Gly
65                  70                  75                  80

Glu Thr Gly Asp Val Gly Met Thr Gly Ala Glu Gly Pro Arg Gly Phe
                85                  90                  95

Pro Gly Thr Pro Gly Arg Lys Gly Glu Pro Gly Glu Leu Gln Thr Leu
            100                 105                 110

Thr Leu Arg Ser Ser Ser Gln Asn Ser Ser Asp Lys Pro Val Ala His
        115                 120                 125

Val Val Ala Asn His Gln Val Glu Glu Gln Leu Glu Leu Ser Gln Arg
    130                 135                 140

Ala Asn Ala Leu Leu Ala Asn Gly Met Asp Leu Lys Asp Asn Gln Leu
145                 150                 155                 160

Val Val Pro Ala Asp Gly Leu Tyr Leu Val Tyr Ser Gln Val Leu Phe
                165                 170                 175
```

-continued

```
Lys Gly Gln Gly Cys Pro Asp Tyr Val Leu Leu Thr His Thr Val Ser
            180                 185                 190

Arg Phe Ala Ile Ser Tyr Gln Glu Lys Val Asn Leu Leu Ser Ala Val
            195                 200                 205

Lys Ser Pro Cys Pro Lys Asp Thr Pro Glu Gly Ala Glu Leu Lys Pro
            210                 215                 220

Trp Tyr Glu Pro Ile Tyr Leu Gly Gly Val Phe Gln Leu Glu Lys Gly
225                 230                 235                 240

Asp Gln Leu Ser Ala Glu Val Asn Leu Pro Lys Tyr Leu Asp Phe Ala
            245                 250                 255

Glu Ser Gly Gln Val Tyr Phe Gly Val Ile Ala Leu
            260                 265

<210> SEQ ID NO 7
<211> LENGTH: 255
<212> TYPE: PRT
<213> ORGANISM: Artificial Sequence
<220> FEATURE:
<223> OTHER INFORMATION: CD40L-ACRP30
<220> FEATURE:
<221> NAME/KEY: DOMAIN
<222> LOCATION: (1)...(8)
<223> OTHER INFORMATION: Flag
<220> FEATURE:
<221> NAME/KEY: DOMAIN
<222> LOCATION: (9)...(16)
<223> OTHER INFORMATION: Linker
<220> FEATURE:
<221> NAME/KEY: DOMAIN
<222> LOCATION: (17)...(108)
<223> OTHER INFORMATION: mouseACRP30 aa 18-111
<220> FEATURE:
<221> NAME/KEY: DOMAIN
<222> LOCATION: (109)...(110)
<223> OTHER INFORMATION: Linker
<220> FEATURE:
<221> NAME/KEY: DOMAIN
<222> LOCATION: (111)...(255)
<223> OTHER INFORMATION: humanCD40L aa 116-261

<400> SEQUENCE: 7

Asp Tyr Lys Asp Asp Asp Asp Lys Gly Pro Gly Gln Val Gln Leu His
1               5                   10                  15

Glu Asp Asp Val Thr Thr Thr Glu Glu Leu Ala Pro Ala Leu Val Pro
            20                  25                  30

Pro Pro Lys Gly Thr Cys Ala Gly Trp Met Ala Gly Ile Pro Gly His
            35                  40                  45

Pro Gly His Asn Gly Thr Pro Gly Arg Asp Gly Arg Asp Gly Thr Pro
            50                  55                  60

Gly Glu Lys Gly Glu Lys Gly Asp Ala Gly Leu Leu Gly Pro Lys Gly
65                  70                  75                  80

Glu Thr Gly Asp Val Gly Met Thr Gly Ala Glu Gly Pro Arg Gly Phe
            85                  90                  95

Pro Gly Thr Pro Gly Arg Lys Gly Glu Pro Gly Glu Leu Gln Gly Asp
            100                 105                 110

Gln Asn Pro Gln Ile Ala Ala His Val Ile Ser Glu Ala Ser Ser Lys
            115                 120                 125

Thr Thr Ser Val Leu Gln Trp Ala Glu Lys Gly Tyr Thr Met Ser Asn
            130                 135                 140

Asn Leu Val Thr Leu Glu Asn Gly Lys Gln Leu Thr Val Lys Arg Gln
145                 150                 155                 160
```

-continued

```
Gly Leu Tyr Tyr Ile Tyr Ala Gln Val Thr Phe Cys Ser Asn Arg Glu
                165                 170                 175

Ala Ser Ser Gln Ala Pro Phe Ile Ala Ser Leu Cys Leu Lys Ser Pro
            180                 185                 190

Gly Arg Phe Glu Arg Ile Leu Leu Arg Ala Ala Asn Thr His Ser Ser
        195                 200                 205

Ala Lys Pro Cys Gly Gln Gln Ser Ile His Leu Gly Gly Val Phe Glu
    210                 215                 220

Leu Gln Pro Gly Ala Ser Val Phe Val Asn Val Thr Asp Pro Ser Gln
225                 230                 235                 240

Val Ser His Gly Thr Gly Phe Thr Ser Phe Gly Leu Leu Lys Leu
                245                 250                 255

<210> SEQ ID NO 8
<211> LENGTH: 254
<212> TYPE: PRT
<213> ORGANISM: Artificial Sequence
<220> FEATURE:
<223> OTHER INFORMATION: humanACRP30-Fas ligand fusion protein
<220> FEATURE:
<221> NAME/KEY: DOMAIN
<222> LOCATION: (1)...(8)
<223> OTHER INFORMATION: Flag
<220> FEATURE:
<221> NAME/KEY: DOMAIN
<222> LOCATION: (9)...(16)
<223> OTHER INFORMATION: Linker
<220> FEATURE:
<221> NAME/KEY: DOMAIN
<222> LOCATION: (17)...(107)
<223> OTHER INFORMATION: Collagen domain aa 18-108
<220> FEATURE:
<221> NAME/KEY: DOMAIN
<222> LOCATION: (108)...(110)
<223> OTHER INFORMATION: Linker
<220> FEATURE:
<221> NAME/KEY: DOMAIN
<222> LOCATION: (111)...(254)
<223> OTHER INFORMATION: hFasL extracellular domain aa 139-281

<400> SEQUENCE: 8

Asp Tyr Lys Asp Asp Asp Asp Lys Gly Pro Gly Gln Val Gln Leu Gln
1               5                   10                  15

His Asp Gln Glu Thr Thr Thr Gln Gly Pro Gly Val Leu Leu Pro Leu
                20                  25                  30

Pro Lys Gly Ala Cys Thr Gly Trp Met Ala Gly Ile Pro Gly His Pro
            35                  40                  45

Gly His Gly Ala Pro Gly Arg Asp Gly Arg Asp Gly Thr Pro Gly Glu
        50                  55                  60

Lys Gly Glu Lys Gly Asp Pro Gly Leu Ile Gly Pro Lys Gly Asp Ile
65                  70                  75                  80

Gly Glu Thr Gly Val Gly Ala Glu Gly Pro Arg Gly Phe Pro Gly Ile
                85                  90                  95

Gln Gly Arg Lys Gly Glu Pro Gly Glu Gly Ala Met His Val Asp Glu
            100                 105                 110

Lys Lys Glu Leu Arg Lys Val Ala His Leu Thr Gly Lys Ser Asn Ser
        115                 120                 125

Arg Ser Met Pro Leu Glu Trp Glu Asp Thr Tyr Gly Ile Val Leu Leu
    130                 135                 140

Ser Gly Val Lys Tyr Lys Lys Gly Gly Leu Val Ile Asn Glu Thr Gly
145                 150                 155                 160

Leu Tyr Phe Val Tyr Ser Lys Val Tyr Phe Arg Gly Gln Ser Cys Asn
```

-continued

```
                165                 170                 175
Asn Leu Pro Leu Ser His Lys Val Tyr Met Arg Asn Ser Lys Tyr Pro
            180                 185                 190

Gln Asp Leu Val Met Met Glu Gly Lys Met Met Ser Tyr Cys Thr Thr
            195                 200                 205

Gly Gln Met Trp Ala Arg Ser Ser Tyr Leu Gly Ala Val Phe Asn Leu
            210                 215                 220

Thr Ser Ala Asp His Leu Tyr Val Asn Val Ser Glu Leu Ser Leu Val
225                 230                 235                 240

Asn Phe Glu Glu Ser Gln Thr Phe Phe Gly Leu Tyr Lys Leu
                245                 250

<210> SEQ ID NO 9
<211> LENGTH: 246
<212> TYPE: PRT
<213> ORGANISM: Artificial Sequence
<220> FEATURE:
<223> OTHER INFORMATION: EDA-Fas ligand fusion protein
<220> FEATURE:
<221> NAME/KEY: DOMAIN
<222> LOCATION: (1)...(8)
<223> OTHER INFORMATION: Flag
<220> FEATURE:
<221> NAME/KEY: DOMAIN
<222> LOCATION: (9)...(16)
<223> OTHER INFORMATION: Linker
<220> FEATURE:
<221> NAME/KEY: DOMAIN
<222> LOCATION: (17)...(99)
<223> OTHER INFORMATION: Collagen domain aa 160-242
<220> FEATURE:
<221> NAME/KEY: DOMAIN
<222> LOCATION: (100)...(104)
<223> OTHER INFORMATION: Linker
<220> FEATURE:
<221> NAME/KEY: DOMAIN
<222> LOCATION: (105)...(246)
<223> OTHER INFORMATION: hFas ligand extracellular domain aa 139-281

<400> SEQUENCE: 9

Asp Tyr Lys Asp Asp Asp Asp Lys Gly Pro Gly Gln Val Gln Leu Gln
1               5                   10                  15

Ser Lys Ser Asn Glu Gly Ala Asp Gly Pro Val Lys Asn Lys Lys Lys
            20                  25                  30

Gly Lys Lys Ala Gly Pro Pro Gly Pro Asn Gly Pro Pro Gly Pro Pro
            35                  40                  45

Gly Pro Pro Gly Pro Gln Gly Pro Pro Gly Ile Pro Gly Ile Pro Gly
        50                  55                  60

Ile Pro Gly Thr Thr Val Met Gly Pro Pro Gly Pro Pro Gly Pro Pro
65                  70                  75                  80

Gly Pro Gln Gly Pro Pro Gly Leu Gln Gly Pro Ser Gly Ala Ala Asp
                85                  90                  95

Lys Ala Gly Met His Val Asp Glu Lys Lys Glu Leu Arg Lys Val Ala
            100                 105                 110

His Leu Thr Gly Lys Ser Asn Ser Arg Ser Met Pro Leu Glu Trp Glu
            115                 120                 125

Asp Thr Tyr Gly Ile Val Leu Leu Ser Gly Val Lys Tyr Lys Lys Gly
            130                 135                 140

Gly Leu Val Ile Asn Glu Thr Gly Leu Tyr Phe Val Tyr Ser Lys Val
145                 150                 155                 160

Tyr Phe Arg Gly Gln Ser Cys Asn Asn Leu Pro Leu Ser His Lys Val
                165                 170                 175
```

Tyr Met Arg Asn Ser Lys Tyr Pro Gln Asp Leu Val Met Met Glu Gly
            180                 185                 190

Lys Met Met Ser Tyr Cys Thr Thr Gly Gln Met Trp Ala Arg Ser Ser
        195                 200                 205

Tyr Leu Gly Ala Val Phe Asn Leu Thr Ser Ala Asp His Leu Tyr Val
    210                 215                 220

Asn Val Ser Glu Leu Ser Leu Val Asn Phe Glu Glu Ser Gln Thr Phe
225                 230                 235                 240

Phe Gly Leu Tyr Lys Leu
            245

<210> SEQ ID NO 10
<211> LENGTH: 18
<212> TYPE: PRT
<213> ORGANISM: Artificial Sequence
<220> FEATURE:
<223> OTHER INFORMATION: Specific Linker

<400> SEQUENCE: 10

Val Asp Leu Glu Gly Ser Thr Ser Asn Gly Arg Gln Ser Ala Gly Ile
1               5                   10                  15

Arg Leu

<210> SEQ ID NO 11
<211> LENGTH: 18
<212> TYPE: PRT
<213> ORGANISM: Artificial Sequence
<220> FEATURE:
<223> OTHER INFORMATION: Specific Linker

<400> SEQUENCE: 11

Val Asp Leu Glu Gly Ser Thr Ser Asn Gly Arg Gln Cys Ala Gly Ile
1               5                   10                  15

Arg Leu

<210> SEQ ID NO 12
<211> LENGTH: 8
<212> TYPE: PRT
<213> ORGANISM: Artificial Sequence
<220> FEATURE:
<223> OTHER INFORMATION: Flag

<400> SEQUENCE: 12

Asp Tyr Lys Asp Asp Asp Asp Lys
1               5

<210> SEQ ID NO 13
<211> LENGTH: 8
<212> TYPE: PRT
<213> ORGANISM: Artificial Sequence
<220> FEATURE:
<223> OTHER INFORMATION: Linker

<400> SEQUENCE: 13

Gly Pro Gly Gln Val Gln Leu Gln
1               5

<210> SEQ ID NO 14
<211> LENGTH: 4
<212> TYPE: PRT
<213> ORGANISM: Artificial Sequence
<220> FEATURE:
<223> OTHER INFORMATION: Linker

```
<400> SEQUENCE: 14

Met His Val Asp
1

<210> SEQ ID NO 15
<211> LENGTH: 51
<212> TYPE: DNA
<213> ORGANISM: Artificial Sequence
<220> FEATURE:
<223> OTHER INFORMATION: A DNA fragment encoding for the signal
      peptide of haemaglutin, including 6 bases in the untranslated
      seqeunce in the 5' region.

<400> SEQUENCE: 15
caaaacatgg ctatcatcta cctcatcctc ctgttcaccg ctgtgcgggg c            51

<210> SEQ ID NO 16
<211> LENGTH: 24
<212> TYPE: DNA
<213> ORGANISM: Artificial Sequence
<220> FEATURE:
<223> OTHER INFORMATION: Flag epitop

<400> SEQUENCE: 16
gattacaaag acgatgacga taaa                                         24

<210> SEQ ID NO 17
<211> LENGTH: 18
<212> TYPE: DNA
<213> ORGANISM: Artificial Sequence
<220> FEATURE:
<223> OTHER INFORMATION: A linker

<400> SEQUENCE: 17
ggacccggac aggtgcag                                                18

<210> SEQ ID NO 18
<211> LENGTH: 63
<212> TYPE: DNA
<213> ORGANISM: Homo sapiens

<400> SEQUENCE: 18
gagaagcact ttgggattct ttccattatg attctttgtt acaggcaccg agatgttgaa  60
gcc                                                                63

<210> SEQ ID NO 19
<211> LENGTH: 10
<212> TYPE: DNA
<213> ORGANISM: Artificial Sequence
<220> FEATURE:
<223> OTHER INFORMATION: Linker sequence of the vector PS 038

<400> SEQUENCE: 19
cagtgtgctg                                                         10

<210> SEQ ID NO 20
<211> LENGTH: 10
<212> TYPE: DNA
<213> ORGANISM: Artificial Sequence
<220> FEATURE:
<223> OTHER INFORMATION: Mutated linker sequence of the vector PS 038

<400> SEQUENCE: 20
cagtctgcag                                                         10
```

-continued

```
<210> SEQ ID NO 21
<211> LENGTH: 8
<212> TYPE: PRT
<213> ORGANISM: Artificial Sequence
<220> FEATURE:
<223> OTHER INFORMATION: Linker

<400> SEQUENCE: 21

Gly Pro Gly Gln Val Gln Leu His
 1               5

<210> SEQ ID NO 22
<211> LENGTH: 4
<212> TYPE: PRT
<213> ORGANISM: Artificial Sequence
<220> FEATURE:
<223> OTHER INFORMATION: Sequence at N-terminus of oligomerization
      domain

<400> SEQUENCE: 22

Gly Gly Cys Cys
 1

<210> SEQ ID NO 23
<211> LENGTH: 8
<212> TYPE: PRT
<213> ORGANISM: Artificial Sequence
<220> FEATURE:
<223> OTHER INFORMATION: Sequence at C-terminus of oligomerization
      domain

<400> SEQUENCE: 23

Ala Arg Thr Pro Gly Gly Gly Ser
 1               5

<210> SEQ ID NO 24
<211> LENGTH: 14
<212> TYPE: PRT
<213> ORGANISM: Artificial Sequence
<220> FEATURE:
<223> OTHER INFORMATION: Linker

<400> SEQUENCE: 24

Pro Gln Pro Gln Pro Lys Pro Gln Pro Lys Pro Glu Pro Glu
 1               5                  10
```

BIMER OR AN OLIGOMER OF A DIMER, TRIMER, QUADROMER OR PENTAMER OF RECOMBINANT FUSION PROTEINS

RELATED APPLICATIONS

This is a continuation under 35 U.S.C. 111(a) of International Application No. PCT/EP00/13032 filed Dec. 20, 2000 and published in German as WO 01/49866 A1 on Jul. 12, 2001, which claimed priority under 35 U.S.C. 119 from German Application No. 199 63 859.4, filed Dec. 30, 1999, which applications and publication are incorporated herein by reference.

The present invention concerns bimers or oligomers of bimers, trimers, quadromers or pentamers of recombinant fusion proteins, whereby the recombinant fusion proteins have at least one component A and one component B. In addition, the present invention concerns the use of bimers or oligomers of these types to manufacture a drug and/or their use for in-vitro diagnosis. Finally, the present invention also concerns fusion proteins that have one component A and one component B, whereby the component B contains a multimerizing and oligomerizing segment, or a functional derivative of a segment of this type of a protein, selected from the group consisting of the family of C1q proteins or the collections. DNA sequences that encode for a fusion protein of this type and expressions vectors and host cells which contain the DNA sequence and/or the expression vector are also the subject of the present invention.

Proteins, which occur physiologically as dimers, trimers, quadromers or pentamers, are found in great numbers in nature. Because of the interactions at the surfaces of these proteins which dimerize or multimerize in solution, there may be spontaneous aggregation of proteins or even, as well, for example, aggregation that is kinetically delayed because it is dependent on the concentration or the milieu. The causes of this are hydrophobic interactions, hydrogen bond formations and/or coulomb forces.

However, together with this, structure motives are found with certain proteins that lead to the formation of specific structural supersecondary structures and thus to protein dimers or multimers. The formation of supersecondary structures is based on characteristic amino acid sequences of the proteins that form these dimers or multimers. "Coiled-coil helices" might be referred to as supersecondary structures, for example, which effect a dimerizing or multimerizing of proteins through interactions of characteristic $\alpha$-helices, which occur with each of the proteins that form the coiled-coil form. The coiled-coil helix as an intermolecular "dimerizing or multimerizing domain" of proteins exhibits structurally a super helix with two or more helices coiled around themselves. These types of coiled-coil motives are found in particular with extracellular protein dimers or multimers, and in particular with proteins or protein complexes of the connective tissue.

Beck et al. (J. Mol. Biol. (1996) 256, 909-23) for example describe a connective tissue protein, the so-called cartilage matrix protein (CMP), whose aggregation to a homotrimer on triple helix, which is the result of the aggregation of three complementary helices (each as components of a polypeptide), is based on the coiled-coil pattern. Characteristic for the amino acid sequence of a helix of this type forming a triple helix is the heptad pattern $(abcdefg)_n$. The latter's amino acids in the positions a and d usually carry nonpolar side chains and thus permit the formation of the superhelical structure described above, here as a triple helix made of three helices.

In addition, the literature also states that with another extracellular matrix protein (cartilage oligomeric matrix protein) (COMP) there are in fact five helices in the form of a five-coil coiled-coil helix that interact with one another and thus are able to form pentamers. (Kajava, PROTEINS: Structure, Function and Genetics, 24:218-226 (1996); Malashkevich et al., Science, Vol. 274, 761-765, 1996).

Along with the matrix proteins COMP and CMP, which do not belong to the proteins from the collagen family, specific structural multimerizing phenomena through the formation of supersecondary structures are also found with proteins from the collagen family. Here the structure of collagen fibres is characterized by the tropocollagen that consists of three helically twisted polypeptides. The protofibrilla of a hair is also developed from a triple helix of $\alpha$-keratin with the motive "coiled-coil", although in this case left-handed.

To increase the avidity of ligands, Terskikh et al. (PNAS, Vol. 94, 1663-1668, 1997) suggested using fusion proteins with a short peptide with ligand function and the "coiled-coil" domain of the matrix protein COMP. An increased avidity could be verified for these pentamers, whereby aggregates of a higher order cannot be obtained in this way.

In addition, because of their sequence homologies in their respective multimerizing sequence sections, the proteins C1q, collagens $\alpha 1$ (X), $\alpha 2$ (VII), the hibernating protein, ACRP30, the internal ear structure protein, cerebellin and multimerin as protein family are brought together under the designation C1q family (Kischore and Reid, Immunopharmacol., 42 (1999) 15-21), which is found structurally as dimers or multimers. Among the proteins with multimerizing characteristics occurring in this family, for example, the structure of the protein C1q, which is familiar from the complement system, is characterized by monomers which each have a globular, so-called head domain, and a "collagen-like" helical sequence section. The monomers trimerize through this helical sequence section, which forms a coiled-coil triple helix. Six of these C1q trimers themselves form an oligomer, whereby the oligomerizing of the protein trimers is based on interactions between the individual coiled-coil triple helices. The result is that this structural arrangement in the protein or the multimerized (oligomerized) protein complex C1q leads to a structure referred to as a "bouquet", whereby it is ensured that 18 globular, C-terminally arranged head domains are linked to a hexamer of trimers.

A similar structure as with protein C1q can be also seen in the protein ACRP30, which is also a protein from the C1q family (Hu et al., J. Biol. Chem., Vol. 271, No. 18, 10697-10703, 1996). This serum protein, which is secreted by adipocytes, is in all probability quadromers of trimers, whereby, as with the C1q protein, globular C-terminal domains are linked via triple helices similar to collagens. Probably four of these triple helices finally form an oligomer themselves through corresponding interactions. In the publication by Shapiro and Scherer (Current Biology 1998, 8:335-338) the structure of a homotrimer of ACRP30 is shown that was determined with the help of X-ray structural analysis.

In addition, proteins from the class of the collectins are known from the literature which are characterized by a collagen-like domain, a neck region and in addition by a globular carboxyterminal lectin-binding domain. The collectins also occur physiologically as oligomers of trimers. For example, the lung surfactant protein A (SP-A) and the mannose binding protein (MBP), both of which are from the family of collecting, trimerize through the interactions of their "collagen-like" domains and are finally found as hexamers of trimers (Epstein et al., Current Opinion in Immunology, Vol. 8, No. 1, 1996, 29-35). Accordingly, the proteins known under the designation of collectins form oligomers (e.g. hexamers) of multimers (e.g. trimers). The literature also shows that numerous proteins that have a physiological effect as signal molecules can only transduct a biological signal under certain conditions. For example, membrane bound FasL is biologically, i.e. apoptotically, effective, whereas after the cleaving of the extracellular protein segment (so-called FasL) this non-membrane-bound sFasL fraction can no longer bring about an apoptotic effect on target cells. The publication by Schneider et al. (J. Exp. Med., Vol. 187, No. 8, 1998, 1205-1213) states that the biological effect of sFasL trimers which, as explained previously, are obtained after cleaving from membrane-bound protein segment, can in fact be reactivated with regard to their physiological function through the use of crosslinking antibodies. For this purpose a fusion protein was constructed that consists of the trimerizing domain of FasL, a short linker sequence and a flag marking (with the flag amino acid sequence (single-letter code) DYKDDDDK), expressed, and this type of fusion protein which is non-structurally trimerized (i.e. not through specific secondary structure interactions with the result of the formation of a supersecondary structure) was crosslinked through antibodies directed against the flag tag.

This type of sFasL molecules crosslinked through antibody binding displays a significant increase of the specific apoptotic activity as against non-crosslinked sFasL trimers. This procedure, which is suggested by Schneider et al., does however have the disadvantage that, along with the recombinant, non membrane-bound FasL proteins with the trimerizing domain, specific antibodies also have to be used, in other words, an increase in biological activity can only be achieved through the provision of an additional molecule fraction. In addition, with the theory suggested by Schneider et al. it is not possible to ensure an exactly preset or determinable degree of oligomerizing of the multimers. The antibodies can namely have the effect that the FasL trimers associate to dimers or even that a wide spectrum of oligomerized complexes through to huge sFasL/antibody aggregates occurs. Because an exactly defined product with maximum efficacy is required, for example for medical applications, the result is that the way proposed by Schneider et al. for reactivating and/or increasing sFasL activity, is not practical.

A central object of the present invention is therefore to provide compounds which avoid the disadvantages of the state of the art, in particular which display increased biological activity or bring about a reactivation of the biological activity.

The present object is solved by the subject-matter of claim 1, namely bimers or oligomers of a dimer, trimer, quadromer, or pentamer of recombinant fusion proteins, in that the recombinant fusion proteins have at least one component A and at least one component B, whereby component A covers a protein or a protein segment with biological function, in particular with a binding function, and component B covers a protein or a protein segment which bimerizes or oligomerizes the dimer, trimer, quadromer, or pentamer of a recombinant fusion protein with biological function without the effect of tertiary molecules, or aggregates fusion proteins to dimers or multimers and at the same time links these dimers or multimers together to a bimer or oligomer without the effect of tertiary molecules.

In the representation of the present invention the terms dimer, trimer, quadromer, or pentamer are summarized under the designation multimer and this will be understood as protein complexes from two, three, four or five associated polypeptides (proteins). In contrast, the aggregates of the next higher order, that is, the aggregations of two or more dimers, trimers, quadromers, or pentamers in the above sense are referred to as bimers or oligomers. Proteins or protein segments with biological functions (component A in the fusion protein) are understood in particular to be proteins which have a ligand function, particularly for antibodies or receptors (i.e. can occur in interaction as a binding partner with one or more molecules), modified amino acid sequences, e.g. amino acid sequences with covalent or non-covalent coupled effective agents (possibly of a organic-chemical nature), antibodies or segments of antibodies with paratopes or even hormones, for example, peptide hormones. In particular, the present invention encompasses amino acid sequences of signal proteins as component A in the fusion protein which are biologically already active as monomers and whose effect is increased accordingly as components in a complex according to the present invention, or which only become active through the multimerizing or oligomerizing initiated in accordance with the present invention or through the oligomerizing initiated exclusively in accordance with the present invention (in so far as component A of the fusion protein is already found as a trimer). With physiologically membrane-bound signal proteins, e.g. with TNF cytokines, cleavage products are preferred which contain the extra-membranous, in particular the extra-cellular, protein segments. But amino acid sequences which can function as antigens can also be used as component A in a recombinant fusion protein. Finally, receptors, e.g. receptors from the TNF receptor family, e.g. belonging to the family of type I membrane proteins (e.g. FasR), or segments or derivatives of such receptors, can also be used as component A, which also have a binding function (i.e. interact as a binding partner with another molecule) and therefore fall under the term "ligand" within the meaning of the present invention. These types of capable of binding fragments of biological receptors are suitable in particular for use as drugs, if the complementary biological ligand is found in the patient in non-physiologically high concentrations.

In a preferred embodiment the components A can have the multimers found in the oligomers in accordance with the present invention, i.e., dimers, trimers, quadromers, or pentamers, identical components A (oligomers of homodimers or homomultimers) or different components A (oligomers of heterodimers or heteromultimers). In this way, proteins with different components A, possibly also with a different biological function, can be linked together in dimers or multimers of oligomers in accordance with the present invention. The individual heterodimers or heteromultimers aggregated in the bimers or oligomers can also be the same or different, i.e. a bimer or oligomer in accordance with the present invention may also be composed of different heterodimers or heterooligomers.

However, it is also possible that the fusion proteins in the respective dimer or multimer as a subunit of the bimer or oligomer are identical, but, on the other hand, the individual subunits in the bimer or oligomer arranged as a dimer or multimer are different (heterobimer or heterooligomer of homodimers, homotrimers, homoquadromers or homopentamers). In this way, for example, up to six homotrimers that are different with regard to component A can be associated in a hexamer of trimers in accordance with the present invention. In this way, typically precisely modulated biological activities can be brought about by the selection, the arrangement, the specific combination and/or through the number of components A in the bimer or oligomer. It is known that certain biological effects bring about the desired biological effect, e.g. a cell activation, only through the interaction of at least two ligands (in the biological sense, not in the extended meaning in accordance with the present invention). This is desirable, e.g. with the combination of certain interleukins with regard to the effect as T-cell or B-cell activators. In accordance with the present invention, effectors of this type which are only effective in combination can be arranged in a complex in accordance with the present invention. However, it is also conceivable that compositions will be provided that, for example with regard to the respective component A, contain different oligomers.

In another preferred embodiment the component A in a recombinant fusion protein is a peptide hormone, a growth factor, a cytokine, an interleukin or a segment of these, preferably a segment capable of binding. However, functional derivatives of the above-mentioned peptides and/or proteins can also be used as component A in the recombinant fusion protein which is a component of an oligomer in accordance with the present invention.

Proteins in particular which maintain the biological function, but at the same time have sequence differences to the corresponding native sequences, are described as functional derivatives of biologically active proteins protein segments or peptides. The sequential deviations may be one or more insertions, deletions or substitutions, whereby a sequence homology of at least 70% is preferred and a sequence homology of at least 85% between the derivative used and the native sequence is particularly preferred. Those amino acid sequences in particular come under the term "functional derivatives" which display conservative substitutions as against the physiological sequences. Conservative substitutions are taken to be those substitutions in which amino acids which come from the same class are substituted for one another. There are in particular amino acids with aliphatic side chains, positively or negatively charged side chains, aromatic groups in the side chains, or amino acids whose side chains can be part of hydrogen bonds, for example, side chains with a hydroxy function. This means that, for example, an amino acid with a polar side chain is replaced by another amino acid also with a polar side chain, or, for example, an amino acid characterized by a hydrophobic side chain is substituted by another amino acid which also has a hydrophobic side chain (e.g. serine (threonine) by threonine (serine), or leucine (isoleucine) by isoleucine (leucine).

In accordance with the present invention a ligand is understood to be all molecules that take part in binding reactions. A ligand can therefore be a protein that is normally described as a receptor. A receptor of this type can also be a "ligand" within the meaning of the present invention if it binds a signal molecule.

Under the present invention, oligomers of trimers of recombinant fusion proteins are preferred, in particular trimers for quadromers of trimers (3×3 or 4×3) or hexamers of trimers (6×3).

Particularly preferred is a bimer or oligomer of a dimer, trimer, quadromer, or pentamer of recombinant fusion proteins when component A in the recombinant fusion protein is a cytokine from the TNF cytokine family, a segment of this type of TNF cytokine or a functional derivative of a TNF cytokine or of a corresponding TNF cytokine segment. Here the TNF cytokines that are used can lead to, for example, apoptotic, proliferating or activating effects in the target cells by binding to the corresponding receptors. In a non-exhaustive list, the proteins CD40L, FasL, TRAIL, TNF, CD30L, OX40L, RANKL, TWEAK, Lta, Ltab2, LIGHT, CD27L, 41-BB, GITRL, APRIL, EDA, VEGI and BAFF can in particular be considered for use as TNF cytokines. Extracellular segments of the above-mentioned membrane-bound TNF-cytokines or other functional derivatives are preferred for use as component A in recombinant fusion proteins. These cleavage products are particularly preferred when their respective biological functionality, in particular their capacity for binding to the respective receptor, is retained. Functional derivatives in the above sense of the above-mentioned TNF cytokines or segments of TNF cytokines can also be used as component A of the fusion protein. In a particularly preferred embodiment, component A of the recombinant fusion protein is chosen from the group consisting of hFasL (AA 139-261), hTRAIL (AA 95-281), hCD40L (AA 116-261) and m or hTNFα (AA 77-235).

In addition, receptors (membrane-bound or extracellular), in particular receptors of proteins of the family of the TNF cytokines, in particular the physiological receptors of the above-mentioned TNF cytokines or segments or derivatives of the receptors are used in a preferred embodiment as component A in the recombinant fusion protein. In the event that segments of receptors are used as component A these will in particular be segments of the physiological protein sequence of these types of receptors which are arranged physiologically extra-membranously. The extracellular segments of these type of receptors come in particular into consideration here. For example, in accordance with the present invention the binding domain(s) of a receptor, in particular of a receptor which binds a cytokine from the family of the TNF cytokines (e.g. FasR, CD30, CD40, GITR, TNF-R1 and/or TNF-R2), can be provided on a dimerizing immunoglobulin (dimerizing Fc fragment) and these dimers can themselves be bimerized or oligomerized to bimer or oligomer complexes in accordance with the present invention through a component B, for example a collagen-like segment with the capability of bimerizing or oligomerizing dimers or multimers. For this purpose, for example, a tetramer of dimers or multimers (e.g. through tetramerizing segments of ACPR30) may be considered, or a pentamer of dimers or multimers (e.g. through corresponding sequence sections of a monomer from the COMP complex used as component B) or even a hexamer of dimers or multimers (e.g. through hexamerizing segments from monomers of the C1q complex).

Under the present invention the following possibilities are given: the component A which is selected for a recombinant fusion protein, which is to become a component of an oligomer in accordance with the present invention, is already found as such in solution as a dimer or multimer. The component B in such a case will only intensify the dimerizing or multimerizing of component A and will essentially lead to the bimerizing or oligomerizing of the recombinant fusion proteins. This situation is found, for example, if, as component A, at least one TNF ligand or a segment or derivative of the same, which is already typically trimerized in solution, is to be oligomerized as component(s) of a fusion protein. However, in the event that component A as such in solution does not show any dimerizing or multimerizing mediated by surface interaction, in accordance with the present invention component B must ensure not only dimerizing or multimerizing of component A but also bimerizing or oligomerizing of the dimerized or multimerized recombinant fusion proteins. This is typically necessary, for example, for the case that receptors are segments thereof form the component A in the recombinant fusion protein.

In the framework of the present invention bimers or oligomers of dimers, trimers, quadromers, or pentamers of recombinant fusion proteins are disclosed in which component A is preferably an antigen or a segment of an antigen. It is desirable here to use antigens from viral, bacterial or protozoological pathogens. These may be any typical antigen of a pathogen, for example, protein segments and/or specific carbohydrate structures, but they are typically surface antigens of the respective pathogens or segments of surface proteins of pathogens which also display antigenic properties. For example, the following non-exhaustive examples might conceivably be used: haemagglutinin, neuraminidase, PreS1, PreS2, HBs antigen, gp120, gp41 or even typical tumour antigens.

In a preferred embodiment component A of the recombinant fusion protein may also be an amino acid sequence which is suitable for acting as a carrier for a receptor agonist or receptor antagonist. For example, a small organic-chemical molecule active as a pharmacological agent can be typically coupled covalently to this type of amino acid sequence, for example through an ether bond to threonine or serine, an amid-like bond or through an ester bond. Through the present invention large oligomer complexes of for example 18 fusion proteins (e.g. 3×6 fusion proteins) are made available each with connected receptor agonists or receptor antagonists. In this way, it is possible, to achieve a considerable improvement of the efficacy or of the avidity of these types of organic-chemical molecule at their respective receptors, placed on a bimeric or oligomeric protein carrier, for example for use as a drug in human or veterinary medicine.

Component B of the recombinant fusion proteins, which is found dimerized or multimerized in the bimer or oligomer, is typically a protein from the family of the C1q proteins or the collecting. Particularly preferred are the proteins of the C1q proteins or the collectin family as a component of the recombinant fusion proteins, namely as component B if only their dimerizing/multimerizing sequence or bimerizing/oligomerizing sequence in the recombinant fusion protein is transcribed or translated. The mainly globular head domains (FIG. 14), which are contained in the sequence of native monomers, will therefore, as a translation product, not appear in the recombinant fusion protein in accordance with the present invention and are therefore not a component of component B in this protein. The above-mentioned component B in a recombinant fusion protein in accordance with the present invention will show a sequence which typically mainly overlapping has the functionality for dimerizing/ multimerizing or bimerizing/oligomerizing respectively, because the collagen-like segments of the proteins of the above-mentioned families used as component B participate typically in the formation of, for example, triple helices, which themselves have the capability to enter into a bimer or oligomer structure (for example, a tetramer or hexamer of, for example, triple helices) with other triple helices.

Typically therefore the multimerizing and oligomerizing fusion protein will have as component B the domains of the proteins from the families of the C1q proteins or collectins which are responsible for the dimerizing and multimerizing and/or the bimerizing and oligomerizing, while their respective head domains are replaced as component A by other proteins or protein segments which also carry out a biological function. The term "recombinant fusion protein" is therefore to be understood in the framework of the present invention as the minimum one component A and the minimum one component B in the recombinant fusion protein being artificially fused, i.e., that a fusion protein within the meaning of the present invention does not correspond to a naturally occurring protein.

Functional, i.e. bimerizing or oligomerizing derivatives of proteins from the C1q family or the family of collecting, or derivatives of segments of the above-mentioned proteins can also be used as component B for the aggregation of recombinant fusion proteins to bimers or oligomers. In this case, for example, the component B will contain the sequence of the protein C1q, MBP, SP-A (lung surfactant protein A), SP-D (lung surfactant protein D), BC (bovine serum conglutinin), CL43 (bovine collectin-43) and/or ACRP30, or the sequence(s) of bimerizing or oligomerizing segments of at least one of the above-mentioned proteins or of functional derivatives of these proteins of or the segments of the functional derivatives. Bimers or oligomers of recombinant fusion proteins are particularly preferred when component B of the recombinant fusion protein is a protein segment of the protein C1q or the protein ACRP30, in particular of a human variant or mammalian variant, more particularly of the murine variant, whereby a respective protein segment of this type typically does not have a globular head domain of the native protein C1q or protein ACRP30.

Figure 6B:
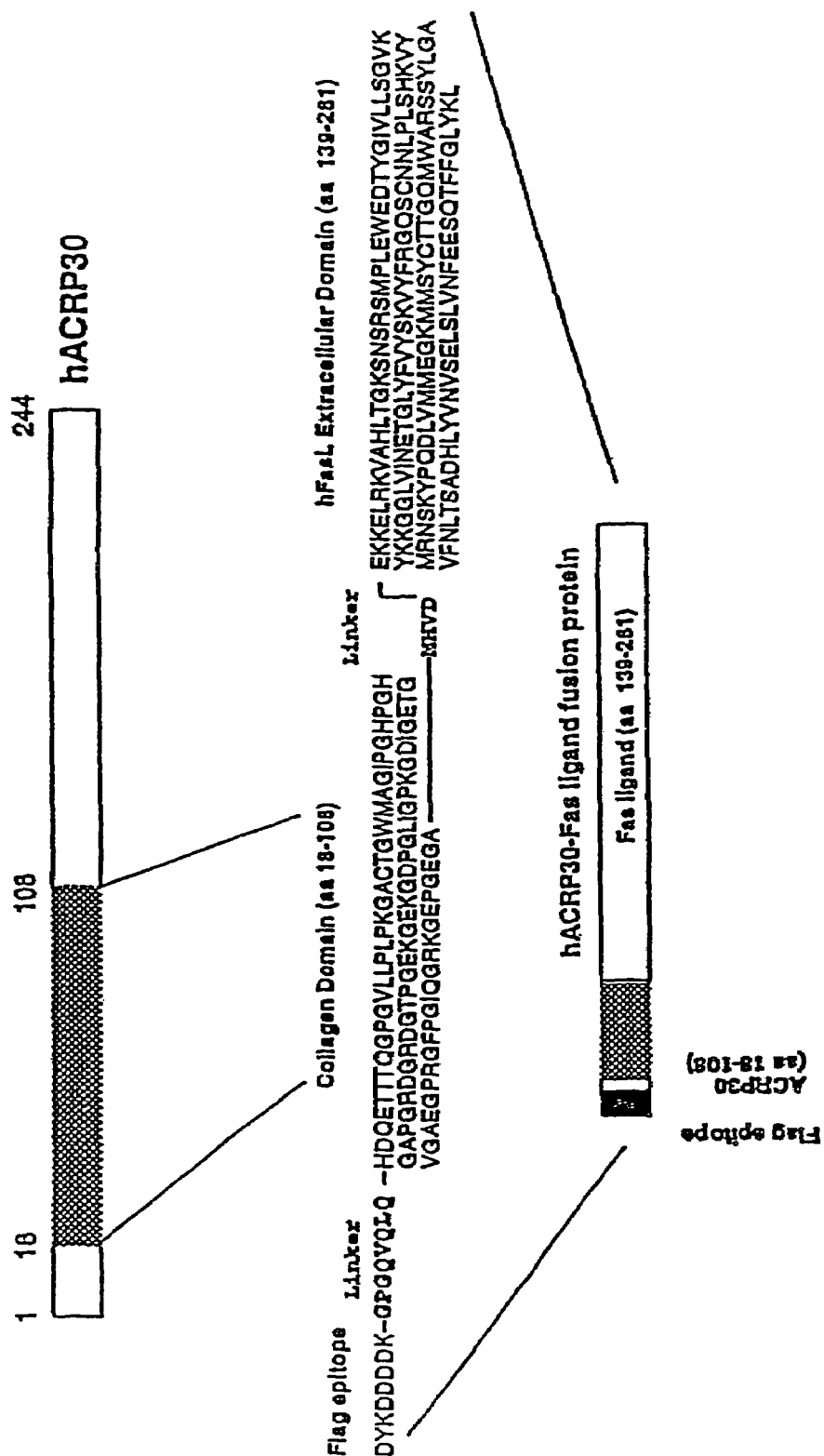

An extremely preferred embodiment of the present invention is represented by bimers or oligomers of dimers, trimers, quadromers, or pentamers of recombinant fusion proteins whose component B contains an amino acid sequence in accordance with FIG. 6A (framed sequence) or FIG. 6B or a functional derivative of this/these amino acid sequence(s) and/or a segment of this/these sequence(s). Typically, this sequence is a segment of the protein mACRP30 (m: murine), e.g. with the amino acids 18 to 111, or a segment of the human variant (hACRP30), e.g. with amino acids 18 to 108. In particular, according to the present invention a fusion protein can therefore be provided whose components A and B are of human origin such that possible immune reactions in humans can be ecxluded during therapeutical application.

Particularly preferred are bimers of oligomers of dimers or multimers of those fusion proteins that have sequences from different host organisms. Aggregates in accordance with the present invention are extremely preferred if they stem from chimary fusion proteins, whereby component A stems from a different type of animal to component B. It can be advantageous if component A corresponds to an amino acid sequence from a mouse, rat, pig or other vertebrate, in particular from a mammal, or to a functional derivative of the same, and component B is of human origin, or vice versa. E.g. complexes in accordance with the present invention of those proteins whose component A corresponds to a sequence from a virus, bacterium or protozoon, combined with a component B of human origin, are also preferred. Naturally, the sequences of component A and component B in a fusion protein in accordance with the present invention can also stem from the same type of animal.

In a further preferred embodiment of the present invention the multimerizing and/or oligomerizing of the fusion protein takes place through a short amino acid sequence of more than 6 amino acids, preferably between 8 and 20 amino acids, which is present in the recombinant fusion proteins as component B. The bimerizing or oligomerizing of fusion proteins, which are already found as such not through supersecondary structures but through surface interaction in solution as dimers or multimers, which is typically achieved through this short amino acid sequence, is preferably based on the formation of disuiphide bridges, which is possible through the specific amino acid sequence in the recombinant fusion protein. This means that component B preferably has at least one cystein, which under oxidizing conditions can form a covalent link with the at least one cystein of a fusion protein of at least one other dimer or multimer. The amino acid sequence (single-letter code) VDLEGSTSNGRQCA-GIRL (SEQ ID NO:11) would be an example of the preferred case that component B contains a short bimerizing or oligomerizing amino acid sequence of between 8 and 20 amino acids. This sequence of 18 amino acids has a cystein residue at position 11 which can form a disulphide bridge between the dimers or multimers.

Functional derivatives or segments of these 18 amino acids containing sequences can be used as component B. Here the sequence VDLEGSTSNGRQSAGIRL (SEQ ID NO:10) should be mentioned in particular, which, although the cystein residue at position 11 has been substituted by senile residue, can still ensure bimerizing or oligomerizing of the fusion protein multimers.

The fusion proteins can be arranged in a preferred embodiment in such a way that aggregates of a higher order can be formed beyond the bimerizing or oligomerizing of dimerized or multimerized fusion proteins, This higher order aggregates, which themselves comprise two or more bimers or oligomers, can be provided, for example, through antibodies via crosslinking. The antibodies are directed against epitopes on the fusion protein(s) of a complex in accordance with the present invention, preferably against an epitope of component B. However, together with component A and component B the fusion protein can also have additional sequence sections which serve as antigens for the crosslinking antibodies. In this context, so-called tag sequences are preferred in the framework of the present invention, for example a flag tag, in other words the amino acid sequence DYKDDDDK, or also, for example, a His tag (containing several consecutive histidines).

However, special preference in accordance with the present invention is given to the provision of aggregates of a higher order through more than one component B being contained in the recombinant fusion protein. Preferably, for the formation of aggregates of a higher order, the fusion protein will contain a component B1 for the formation of bimers of oligomers and in addition at least one other component B (preferably a component B2) which is typically different from component B1. The component B2, which must be found in at least one fusion protein of a bimer or oligomer in accordance with the present invention, ensures that the bimers or oligomers form aggregates of a higher order. For example, component B1 can be a bimerizing or oligomerizing segment of a protein from the family of the C1q or collectin proteins, while component B2 is a sequence with 8 to, for example, 28 amino acids which forms at least one disulphide bridge. In the event that at least one disulphide bridge is formed between two different oligomers, a higher order aggregate in accordance with the present invention will be made available, for example a bimer of an oligomer.

In addition, preference will be given to the insertion of so-called linker sequences between component A and component(s) B or, if there are several components B in the fusion protein, between these minimum two components. These linker sequences allow structural separation of the different functional components in the recombinant fusion protein and can preferably take over a "hinge" function, i.e. represent an amino acid sequence with a flexible structure.

This discloses in general in accordance with the present invention bimers or oligomers or aggregates of a higher order which are characterized by an increased biological efficiency and/or through increased avidities at complementary proteins. In this way, as a further subject-matter of the present invention, methods are disclosed which serve the increase of biological efficiency and/or the increase of the avidity of biomolecules or drugs with ligand functions in the sense of the present invention. Methods of this type are characterized by the recombination of at least one component A, which corresponds to a protein or protein segment with biological function, with at least one dimerizing or multimerizing and bimerizing or oligomerizing component B, whereby an increase in the biological activity and/or an increase in the avidity of component A is achieved by the recombinant fusion proteins finally being bimerized or oligomerized through multimerizing and oligomerizing to bimers or oligomers of dimers and multimers. The method is highly preferred when component A is a TNF cytokine, a segment of a TNF cytokine or a functional derivative of such a protein or protein segment. A further preferred method is the recombination of at least one component A with at least one component B into a recombinant fusion protein, whereby at least one component A is a receptor or a segment of a receptor, preferably of a TNF receptor. With regard to preferred embodiments of a method of this kind in accordance with the present invention, the preferred embodiments for the bimers or oligomers described above apply analogously.

The bimers or oligomers of the present invention may be used for the production of a drug or for the treatment of illnesses or disorders in medical use, i.e. for both human and veterinary medicine. The higher order aggregates formed in accordance with the present invention from bimers or oligomers are also suitable for use as drugs or for the production of a drug. A wide range of illnesses or disorders can be treated with bimers or oligomers or with the higher order aggregates claimed in accordance with the present invention. This type of bimers or oligomers or higher order aggregates can be used to produce a drug for the treatment of the following list of illnesses or disorders which is by no means exhaustive: hyperinflammatory disorders, autoimmune diseases, illnesses based on hyperapoptotic or hypoapoptotic reactions, neurodegenerative diseases, but also for treating infectious diseases, tumours, and/or endocrinological disorders. With regard to infectious diseases the use of bimers and oligomers with bacterial or protozoological diseases, but in particular with viral infections, is to be referred to, whereby antibodies or segments of antibodies carrying paratopes are particularly preferred here as component A in the recombinant fusion protein. Bimers or oligomers or their higher order aggregates are specially suitable where the disease makes treatment with biologically active cytokines necessary, for example including for the treatment and/or the production of a drug for the treatment of tumours, in particular of tumours of the lymphatic system.

In addition, the bimers or oligomers in accordance with the present invention will also be used as vaccines or for the production of a vaccine for active or passive immunization against infectious diseases. In the case of active immunization an antigen suitable for vaccination will be used as component A in the recombinant fusion protein. In particular, surface antigens or segments of surface antigens of bacteria, viruses or protozoa, e.g. of plasmodia or trypanosomes, can be used. In a non-exhaustive list, a vaccine which contains bimers or oligomers or aggregates of these, whereby the recombinant fusion proteins must have at least one component A, in other words one or more identical or different antigens of the pathogen, can be used to vaccinate against German measles, measles, poliomyelitis, rabies, tetanus, diphtheria, BCG, tuberculosis, malaria, yellow fever, HIV or influenza viruses, for example rhinoviruses. The combination of different antigens in a bimer or oligomer or a higher order aggregate formed from bimers or oligomers is also possible in accordance with the present invention, whereby different antigens from the same pathogen can be combined in a bimer or oligomer, or antigens from two or more pathogens can be combined in a bimer or oligomer or in a higher order aggregate. Typically, two or more components A1, A2 to AX can be contained in a fusion protein, which is then a component of a bimer or oligomer or of a higher order aggregate in accordance with the present invention, or two or more fusion proteins that are different with regard to at least one component A can be combined in a bimer or oligomer or a higher order aggregate through at least one component B.

Preferably at least two different bimer or oligomer types in accordance with the present invention can also be contained in a composition for use as a drug or as a vaccine, or for their production.

In a further embodiment in accordance with the present invention component A in a fusion protein in accordance with the present invention is an immunomodulator, for example an interleukin (IL), in particular IL-2.

In addition, in the framework of the present invention the use of bimers or oligomers in accordance with the present invention as immunization and/or vaccination adjuvans is disclosed. It is known that many antigens used for immunization trigger only an unsatisfactory immune reaction in the test person. The task of adjuvans is to increase the immunogenic effect. Adjuvans of this type can be used as component A in a fusion protein in accordance with the present invention and therefore as a component of a bimer or oligomer in accordance with the present invention. For example, the component A can contain an amino acid sequence from the CD40 ligand (CD40L) or the sequence or sequence section of an interleukin, for example one of the interleukins 1 to 12. The physiological task of CD40L is to control the transformation of an inactive B cell into the cell cycle. Interleukins, for example IL-4, IL-5, IL-6 and/or CD40L, can be combined in a bimerized or oligomerized complex in accordance with the present invention (different recombinant fusion proteins in a bimer or oligomer), or they can occur as components of a composition (at least two different types of bimer or oligomer, which can each be developed from identical or different fusion proteins) which typically contains at least one, preferably two or more different types of bimer or oligomer in accordance with the present invention, together with the immunogen(s).

The bimers of oligomers, or higher order aggregates as well, of a composition of this type can be composed of fusion proteins which are identical or different with regard to the component(s) A. Hereby, each physiological sequence with co-stimulating characteristics and/or characteristics which activate the immune system (cellular or humoral immune response) can be considered as component A. These may be physiological compounds or synthetic compounds. In this way, compositions are disclosed which contain one or more bimer or oligomer type(s) in accordance with the present invention together with one or more immunogen(s), whereby a bimer or oligomer type in accordance with the present invention can preferably be arranged so that more than one immodulator/immodulator adjuvans is contained in this type of bimerized or oligomerized complex, in other words there is a heterobimer or a heterooligomer. If necessary, a heterobimer or a heterooligomer in accordance with the present invention can bring together not only one or more fusion proteins with an immunogen as component A, but also at least one fusion protein with an adjuvans component as component A, for example CD40L. Two or more different fusion proteins, each with different adjuvans or immunomodulator components, are also conceivable in a heterooligomer in accordance with the present invention. This means that the invention also discloses the use as a drug or as a vaccine in human or veterinary medicine of these types of homoologimer or heterooligomer or of compounds which contain at least one type of heterooligomer or homoologimer in accordance with the present invention.

In the framework of the present invention the bimers or oligomers are used preferably for the production of a drug or for the treatment of the above-mentioned diseases or disorders in such a way that they are suitable for parenteral administration, i.e., for example, subcutaneous, intramuscular or intravenous administration, or even for oral or intranasal administration. The administration of bimers or oligomers or aggregates of these as a vaccine or the basis for the production of a vaccine, will also preferably take place in a parenteral or oral form of administration, but where necessary intranasal as well.

The bimers or oligomers in accordance with the present invention, and/or the higher order aggregates, can be used alone as a medicament or can be included in the production of a medicament. However, they can also be used in combination with other active agent components as a medicament. The bimers or oligomers in accordance with the present invention, and/or the higher order aggregates, can also be combined with pharmaceutically acceptable carriers, auxiliary agents or additives. Appropriate production paths are disclosed in Remington's Pharmaceutical Sciences (Mack. Pub. Co., Easton, Pa., 1980), which is part of the disclosure of the present invention. Examples of carrier materials which can be considered for parenteral administration are sterile water, sterile NaCl solutions, polyalkylene glycols, hydrogenated naphthalenes and in particular biocompatible lactid polymers, lactid/glycolid copolymers or polyoxyethylene/polyoxypropylene copolymers.

The bimers or oligomers in accordance with the present invention, or corresponding higher order aggregates, are also used preferably in the field of in-vitro diagnosis or, for example, for biochemical purifying methods. The use of bimers or oligomers and/or of higher order aggregates of these on purifying columns, which can be packed with these types of complexes, is to be considered. This means that in the framework of the present invention the use of these types of complexes is disclosed for the purposes of detection as well.

In addition, in the framework of the present invention processes are disclosed to produce specifically associated proteins which interaction on the protein surface because of their interaction and as a result are found dimerized or multimerized in solution. In particular with TNF cytokines, or preferably soluble segments of this type of cytokines which trimerize in solution, it is desirable to make them available in a defined stoichiometry in a pure fraction. In the case of a simple coexpression of different proteins which are capable of associating with one another, for example of three different TNF cytokines or different segments of such TNF cytokines, all statistically possible distributions of the coexpressed proteins are found in the trimers associated after expression, in other words, for example, the desired trimers from the proteins P1, P2 and P3, but also trimers from two proteins P1 and a protein P3, etc.

Oligomers in accordance with the present invention can now be used in accordance with the process in order to obtain defined desired heteromultimers, for example, heterotrimers of TNF cytokines or segments of this type of TNF cytokines. For this purpose different fusion proteins are constructed and preferably expressed in a host cell. The fusion proteins expressed here have a component B sequence sections of proteins which form homoologimers from heteromultimers, for example, form a trimer out of three different chains, whereby identical trimers bimerise or oligomerise. Preferably, these components B in the fusion proteins correspond to sequence sections of proteins from the complement or collectin family, for example C1q, which forms homohexamers from heterotrimers. In a fusion protein therefore, a sequence section, which the native protein provides for multimerizing a chain in the heteromultimer, is combined as component B with a component A, for example a TNF cytokine, whereas other fusion proteins (which are to occur in the heterotrimer) each have combinations of another component A, for example a different TNF cytokine or a segment of this, with another sequence section in the native protein, for example a C1q protein, for heteromultimerizing.

The different fusion proteins which can form the heteromultimer are expressed, preferably in a host cell. The heteromultimers combine into homooligomers, because component B can only oligomerize identical heteromultimers. In accordance with the present invention, for example, three different fusion proteins can be expressed, each with a different component A, in other words preferably different TNF cytokines, which each combine either with the multimerizing and oligomerizing α, β or γ chain of C1q. Only heteromultimers with all three TNF cytokines can then be found in the associating oligomers. In contrast, heteromultimers with a different stoichiometry are not found. This means that in accordance with the present invention simply through the selection of the fusion proteins a product can be obtained which is specific in its stoichiometry and not subject to a statistical distribution.

In addition, the use is preferred of such fusion proteins or processes for extracting heteromultimers with the given stoichiometry which have a linker between component A and component B. The linkers are specially preferred when they contain at least one proteolytic cleavage site which permits the components A from the homooligomer complex (of heteromultimers) to be cleaved from the components B. In this way a fraction is obtained which consists exclusively of the desired heteromultimer, for example, a heterotrimer from the different TNF cytokines. The proteolytic cleavage site in the linker is preferably a thrombin consensus sequence.

As a further object of the present invention fusion proteins are described here which are suitable for bimerizing or oligomerizing dimers or multimers, in so far as the recombinant fusion protein contains at least one component A and at least one component B, whereby the component A contains a protein or a protein segment with a biological function, in particular with a ligand function for antibodies or receptors or an antibody or segment of an antibody, and component B contains a dimerizing or multimerizing and bimerizing or oligomerizing segment or a functional derivative of such a segment of a protein, selected from the group consisting of the family of C1q proteins or the collectins. Extreme preference is given to these types of proteins if the component B of the recombinant fusion protein contains a multimerizing and/or an oligomerizing segment of the proteins C1q, SP-A, SP-D, BC, CL43 and ACRP30. A functional derivative of such a segment of the above-mentioned proteins can also be used in the framework of the present invention. In this case, together with component A having biological activity, a fusion protein will typically contain a component B which has exclusively the segment of the above proteins which is responsible for the aggregation, but preferably not the globular "head" domain thereof.

A sequence containing the amino acid sequence of the oligomerizing collagen domain of the ligand EDA, in particular a mammalian variant, more particularly the human variant, or an oligomerizing fragment or functional derivate of such a domain is also considered as component B of a fusion protein according to the present invention. Even more preferred as component B, a sequence segment containing amino acids 160 to 242 of the human EDA protein or a functional derivate, e.g. a fragment, may be used. Preferably it may refer to a hexamer.

A further object of the present invention are DNA sequences which encode for fusion proteins of the type referred to above. This type of DNA sequences is expressed in expression vectors, whereby the corresponding expression vectors, which contain a DNA sequence for the fusion proteins in accordance with the present invention, are also objects of the present invention.

In addition, host cells which are transfected with DNA sequences which code for the fusion proteins in accordance with the present invention also belong to the present invention. Extreme preference in this context is given to host cells which are transfected with expression vectors, whereby the expression vectors again contain DNA sequences which code for the fusion proteins in accordance with the present invention.

A further object of the present invention are receptors, in particular receptors which bind signal molecule ligands from the TNF cytokine family which are found dimerized or multimerized. For example a receptor of this kind, a derivative of the same or a segment of a receptor or of a derivative, in particular a segment which comprises the extracellular region of the receptor, whereby once again the binding domain(s) is (are) preferred, can be found as a component A of a fusion protein which is a component of a dimer or multimer. Dimerizing can be achieved through recombination with segments of immunoglobulins, in particular Fc fragments, whereas multimerizing can be achieved, for example, after recombination with the corresponding multimerizing domains of proteins. For this purpose, all sequence segments of proteins, for example, are suitable which generate dimers or multimers through the formation of supersecondary structures, e.g. coiled-coil helices, or typical collagen-like triple helices (e.g. CMP, COMP, collagen, laminin). Segments of proteins from the C1q family or of collectins are also typically suitable for dimerizing or multimerizing receptors or receptor segments. For example, the extracellular segment of a member of the TNF receptor family, for example the Fas receptor (FasR) as component A in the form of a pentamer, can be expressed as component B through recombination with the corresponding pentamerizing domains of COMP. Here there may be homodimers, heterodimers or heteromultimers of fusion proteins which have a receptor or a receptor segment.

These dimers or multimers of a recombinant protein with a component A containing a receptor or a receptor segment may also be considered as a medicament or for the production of a medicament. Their use is in particular given if increased extracellular concentrations of the corresponding receptor ligands occur in a clinical picture. Here it may also concern increased concentrations of membrane-bound signal molecules, for example TNF cytokines, on the cells themselves, or of soluble signal molecules. However, the use of multimers of this type is in principle also always desirable if the activation of a signal transduction chain, which is triggered on the corresponding typically membrane-bound receptor, is to be prevented or lowered through the use of exogenous soluble dimers or multimers in accordance with the present invention which trap the signal molecules and which consist of fusion proteins which contain a receptor or a receptor segment as component A. The present invention is explained in detail by means of the following figures:

FIG. 1 shows in a single-letter code the amino acid sequence of a recombinant fusion protein in accordance with the present invention (2) occurring in an oligomer (FasL hexamer; (SEQ ID NO:2)) in accordance with the present invention, in other words in the bimer of a trimer. A sequence segement of the hFasL (AA 103 or 139 to 281) is identified as component A, whereas the specific linker (bimerizing in the outcome) with the sequence VDLEGSTSNGRQCAGIRL (SEQ ID NO:11) appears as component B. FIG. 1 also contains the amino acid sequence of the recombinant fusion protein (1) (SEQ ID NO:1) which in accordance with the state of the art only appears as component of a FasL trimer, in other words does not have any component B which bimerizes or oligomerizes the existing multimer, in this case the trimer. The recombinant segments of the two fusion proteins (1) and (2) are marked in FIG. 1 above the sequence details with regard to their respective functionality.

Figure 2:
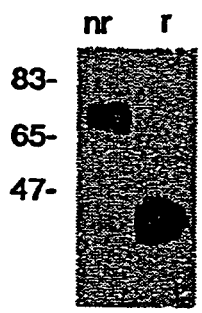
Figure 2:
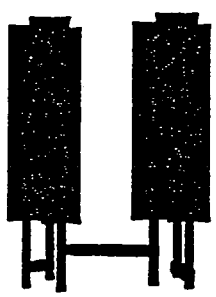

FIG. 2 comprises in FIG. 2A the results of a gel electrophoresis (SDS-PAGE) of fusion proteins in accordance with the present invention (2), therefore with the specific linker sequence (component B), under reducing (r) and non-reducing conditions (nr). Under non-reducing conditions in solution the oligomer is eluted as a native complex of six polypeptides in accordance with the present invention (fusion proteins (2)), because in accordance with the present invention a disulphide bridge is formed between the components B of two fusion proteins (2) in accordance with the present invention, which are each components of different trimers. The result is that there is an oligomer in accordance with the present invention as a FasL hexamer with a molecular weight which appr. corresponds to six times the molecular weight of the fusion protein (2) in accordance with the present invention in monomeric form. If denaturing conditions are present (e.g. on SDS-PAGE), the fusion proteins in accordance with the present invention migrate in the absence of reducing agents as dimers, caused by the formation of a disulphide bridge between two monomers. In contrast, under reducing and denaturing conditions monomers of the fusion protein (2) in accordance with the present invention migrate in the SDS gel. An oligomer in accordance with the present invention, here a bimer of a trimer, of a fusion protein (2) in accordance with the present invention, as shown in FIG. 1, is shown schematically in FIG. 2B.

Figure 3A:
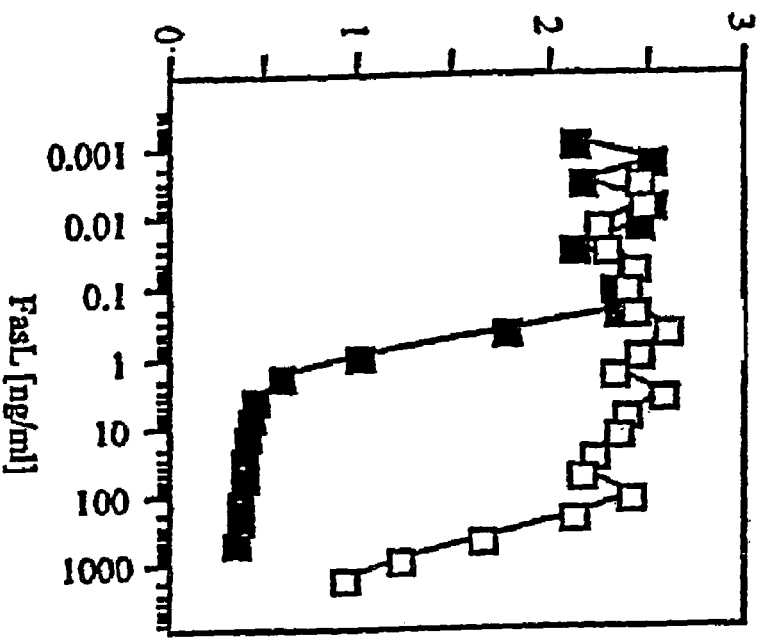
Figure 3A:
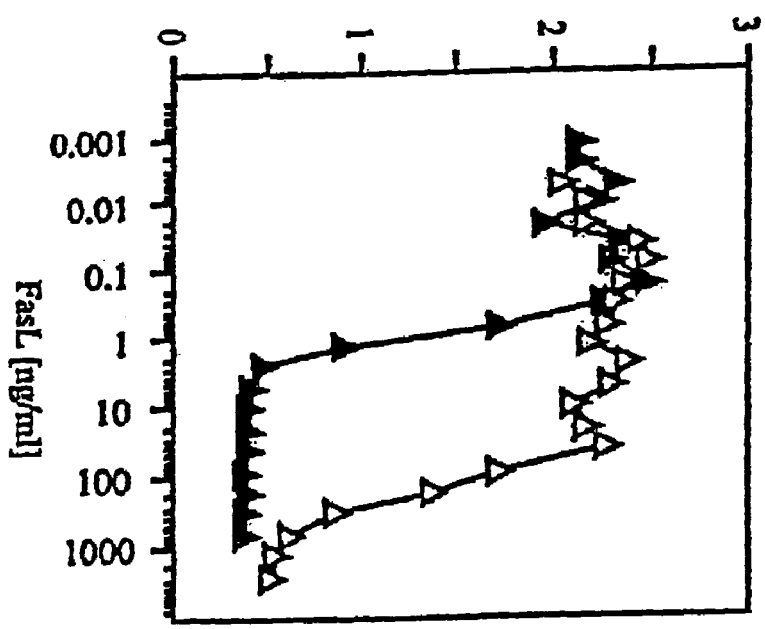
Figure 3B:
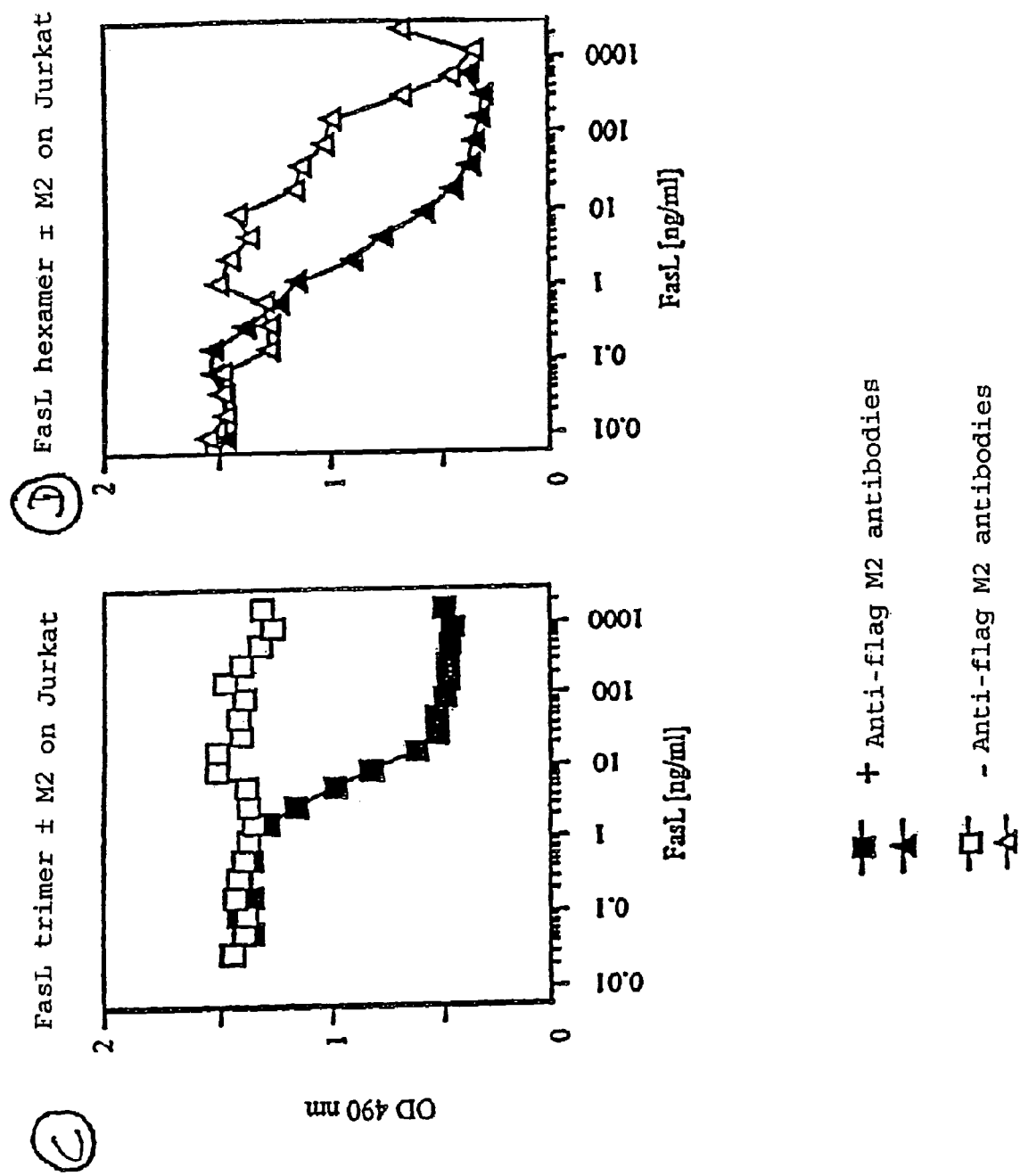

FIG. 3 shows the results of the cytotoxic assay in dependence on the concentrations of FasL trimers (trimers from three fusion proteins in accordance with the state of the art, for example, fusion protein (1) in accordance with FIG. 1 which do not have a component B), or of the FasL bimer (hexamer as bimer of trimers) in accordance with the present invention shown schematically in FIG. 2B in the presence (■, ▲) or absence (□, Δ) of anti-flag M2 antibodies for A20 or Jurkat cells. The optical density at 490 nm is a measure of the viability of the cells (high optical density corresponds to a low apoptotic effect of the added substances and thus a higher viability of the cells). The apoptotic effect on A20 cells (FIG. 3A and 3B) and on Jurkat cells (FIG. 3C and 3D) of FasL bimers of trimers (hexamers) in accordance with the present invention (FIG. 3B and 3D, in each case Δ) increases 3 to 10 times as against the effect of FasL trimers of fusion proteins without a bimerizing or oligomerizing component B (state of the art, FIG. 3A and 3C, in each case □). With additional anti-flag antibodies, which are directed against the flag sequence of the fusion proteins (1) and (2) shown in FIG. 1 and by increasing, for example, the degree of oligomerization of the fusion proteins in accordance with the present invention still further through cross-linking, the apoptotic effect is increased in all preparations (FIGS. 3A to 3D, ■ or ▲ respectively).

Figure 4:
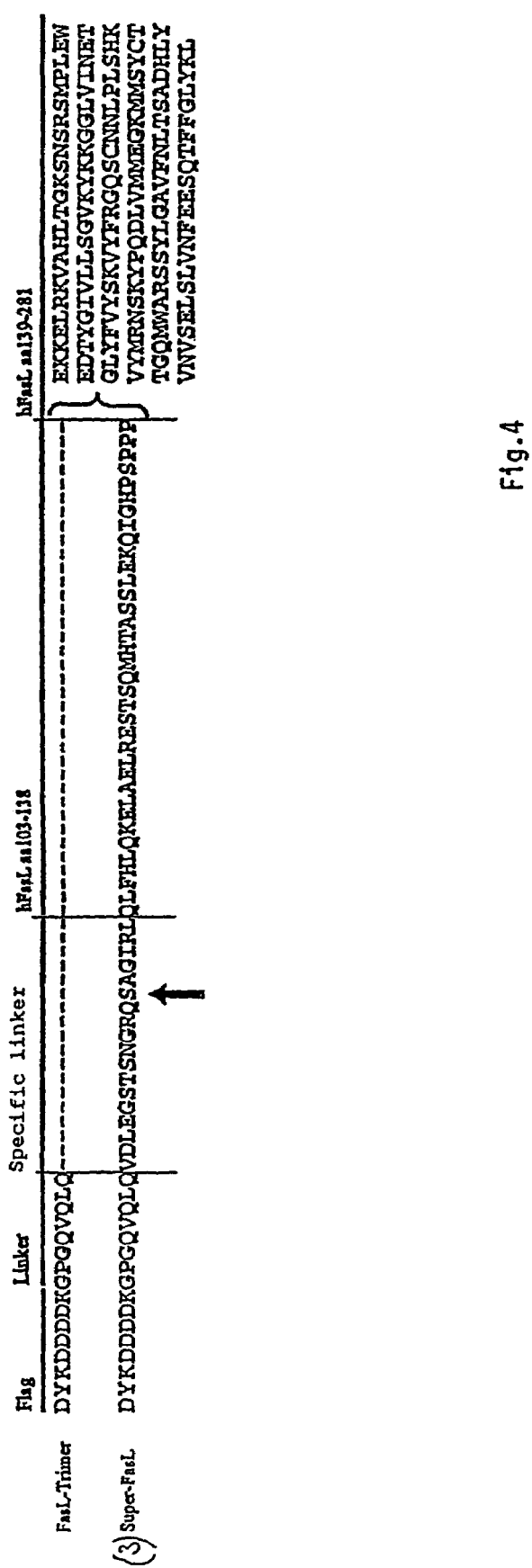

FIG. 4 shows the amino acid sequence (SEQ ID NO:1 and SEQ ID NO:3) of a fusion protein (3) in accordance with the present invention taking into account the (C→S) substitution in the specific linker section (component B of fusion protein (3)) ("super FasL"). See the description of FIG. 1 otherwise. With gel-filtration experiments it was shown that "super FasL" in solution is found in a bimerized form in accordance with the present invention as a hexamer. Under denaturing conditions on SDS-PAGE, fusion proteins (3) in accordance with the present invention migrate, even in the absence of reducing agents, as monomers, because a disulphidc bridge cannot be formed in the linker section because of the amino acid substitution C→S.

Figure 5A:
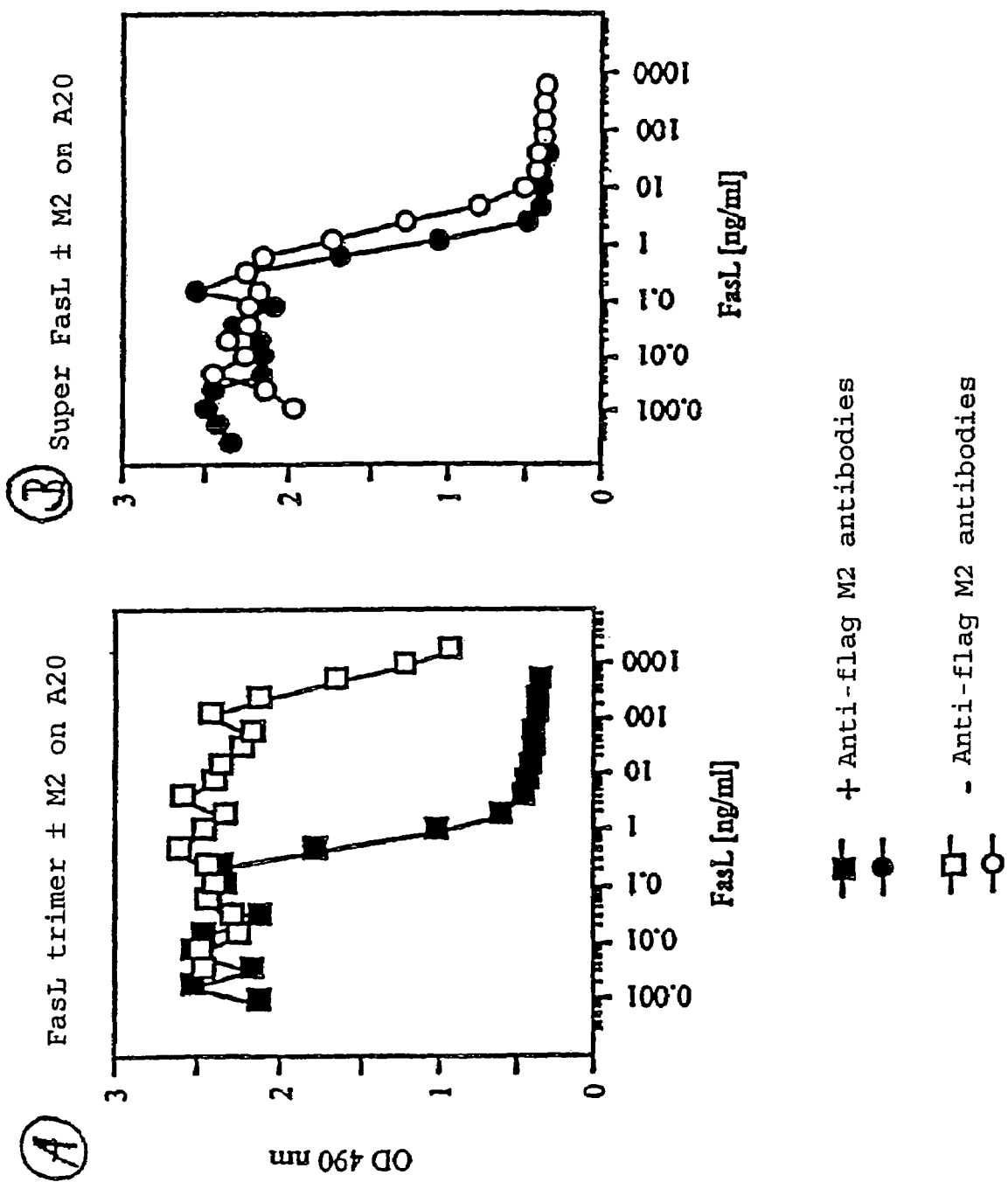
Figure 5B:
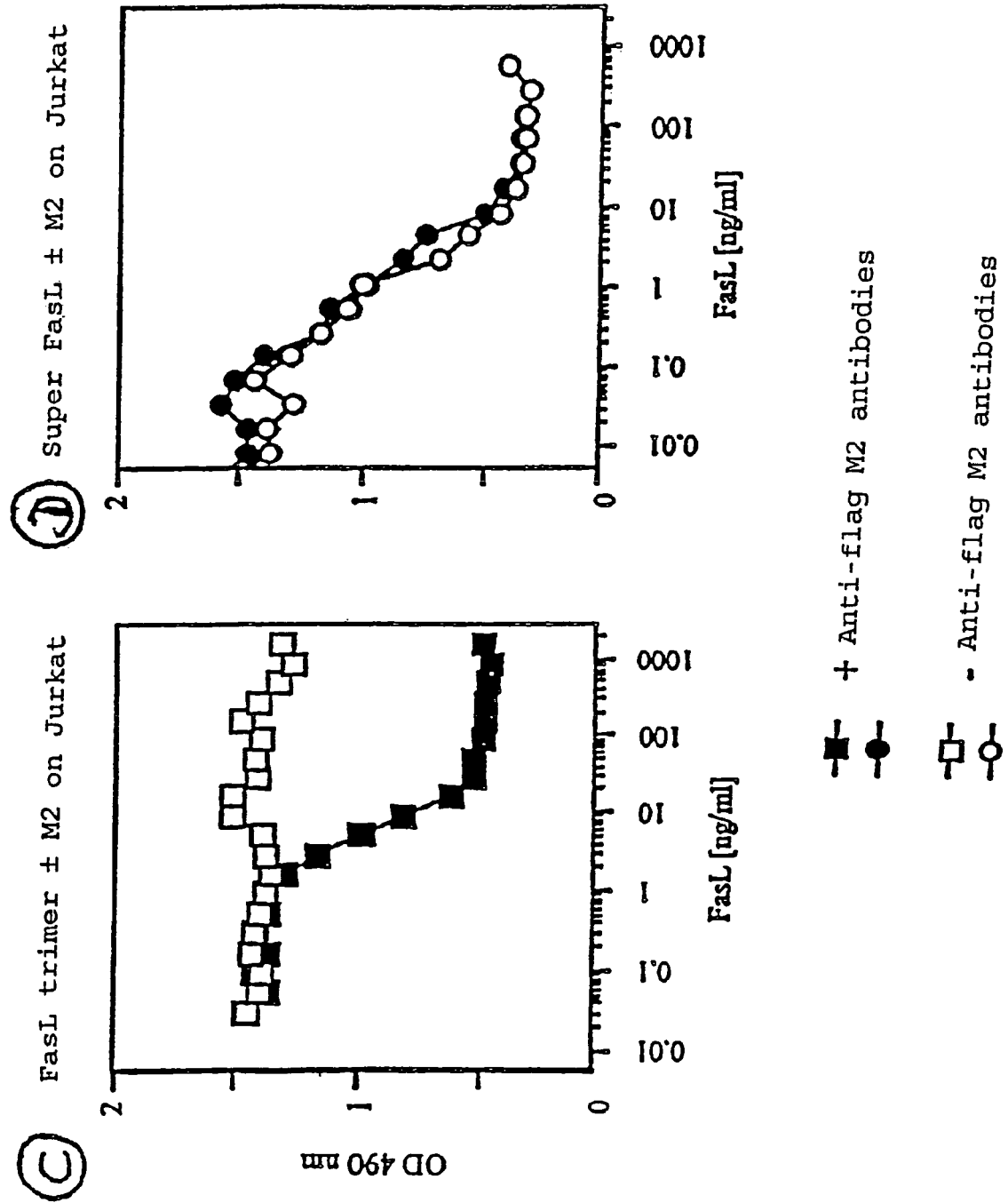

Analogue to FIG. 3, FIG. 5 shows the viability of A20 (FIG. 5B) or Jurkat cells (FIG. 5D) after the addition of aggregates in accordance with the present invention of the fusion protein (3) in accordance with the present invention as shown in FIG. 4 ("super FasL") in the presence (●) or absence (○) of anti-flag M2 antibodies. The fusion proteins (3) in accordance with the present invention bring about an apoptotic effect which is roughly at least 1000 times greater than the effect of FasL trimers (used for control purposes) in accordance with the state of the art without bimerizing or oligomerizing components B (FIG. 5A (A20 cells) and FIG. 5C (Jurkat cell's)) which were used for comparison. The addition of anti-flag M2 antibodies (●) is able to increase the apoptotic activity both on A20 and on Jurkat cells slightly, approx. twice as much, preferably at least 1.5 times, as against the preparation without anti-flag antibodies, by further oligomerisation of "super FasL" to higher order aggregates in accordance with the present invention (FIGS. 5B and 5D). The result of this is that the degree of oligomerisation (here as a bimer of trimers) for the apoptosis triggering, where necessary through oligomerisation on the cell surface, which is brought about through the specific linker of a fusion protein (3) in accordance with the present invention used as component B, is already practically optimum and can be increased slightly by means of higher order aggregates in accordance with the present invention.

FIG. 6A shows the amino acid sequence of a fusion protein (4), FasL-ACRP30 (SEQ ID NO:4), in accordance with the present invention, whereby the fusion protein (4) (in the sequence from the N to the C terminus) has a flag sequence, a linker sequence as component B, the amino acids 18 to 111 of protein mACRP30 (m: murine), the liner LQ and then the amino acids 139 to 281 of hFasL as component A.

FIG. 6B shows a further fusion protein (SEQ ID NO:8). It comprises the collagen domain of the human ACRP30 ligand (hACRP30, with amino acids 18 to 111) whereby the N-terminus thereof is fused to a flag tag DYKDDDDK (SEQ ID NO:12) and the C-terminus thereof to the extracellular domain of human FasL (AA 139 to 281). Between the C-terminus of hACRP30 and hFasL as well as between the Flag tag and the N-terminus of hACRO30 (GPGQVQLQ; SEQ ID NO:13) a linker sequence (MHVD; SEQ ID NO:14) is inserted. All above-mentioned data relate to the one-letter-code of amino acids.

Figure 6C:
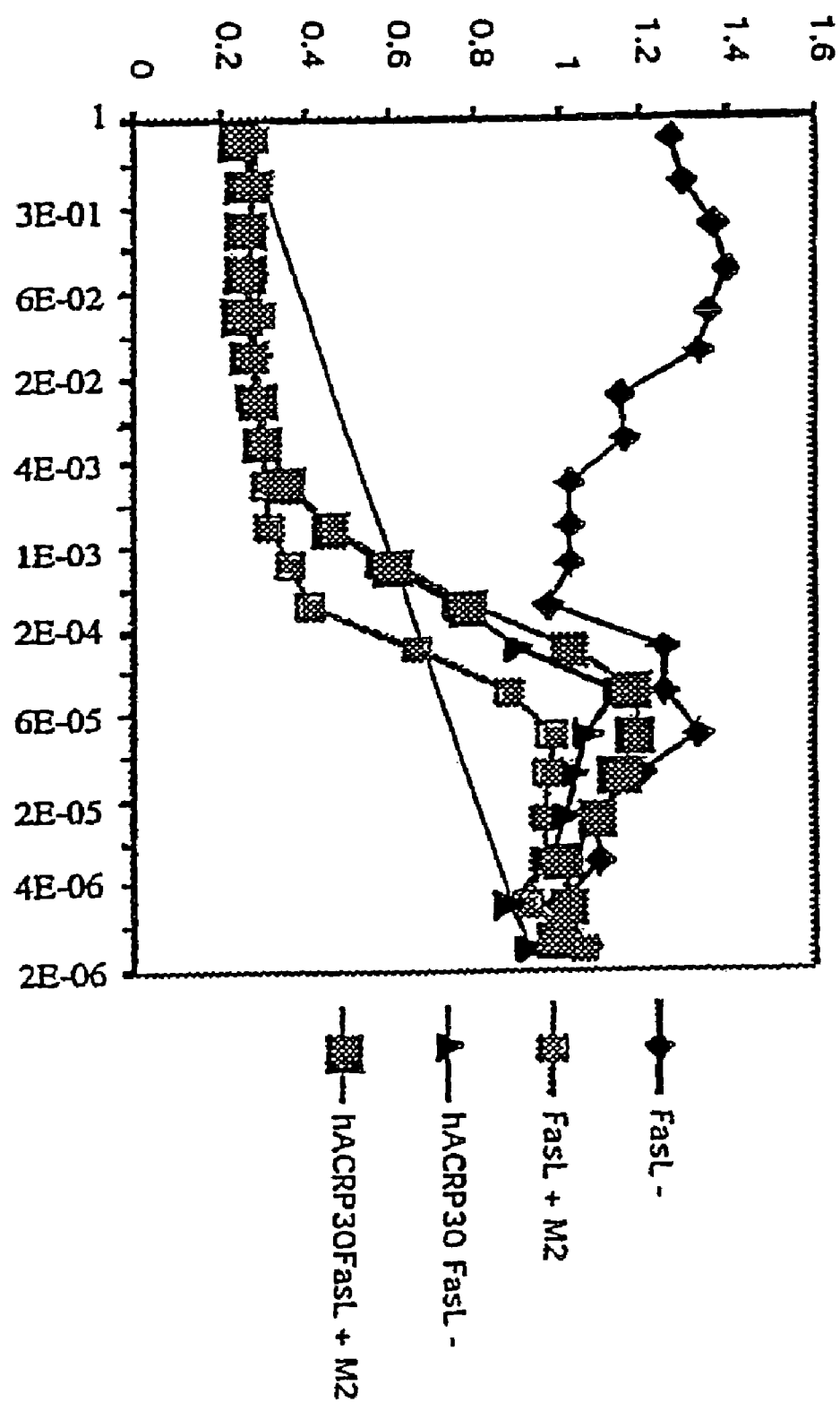

FIG. 6C shows curves resulting from the titration of Jurkat T-cell with FasL on the one hand and with the fusion protein hACRP30/FasL on the other hand, under addition of anti-Flag antibody M2 (+) and without addition of anti-Flag antibody M2 (−). Supernatants (OPTIMEM) of 293-cells, being transiently transfected with FasL or hACRP30/FasL and expressing these proteins, were therefore added to Jurkat T-cells. In successive experiments decreasing concentrations shown on the x-axis of FIG. 6C were employed and the respective viability rate of the Jurkat T-cells was determined by the standard cytotoxicity test described elsewhere. From the graph it is clear that FasL is inactive without crosslinking M2 antibody (♦) and only the crosslinking effect of the M2 antibody causes cytotoxic effects. In contrast thereto, the corresponding effect of a fusion protein according to the present invention, namely hACRP30/FasL, shows already without addition of M2 antibody (▲). The addition of M2 antibodies is hardly able to increase the effect of the fusion protein according to the present invention.

Figure 7:
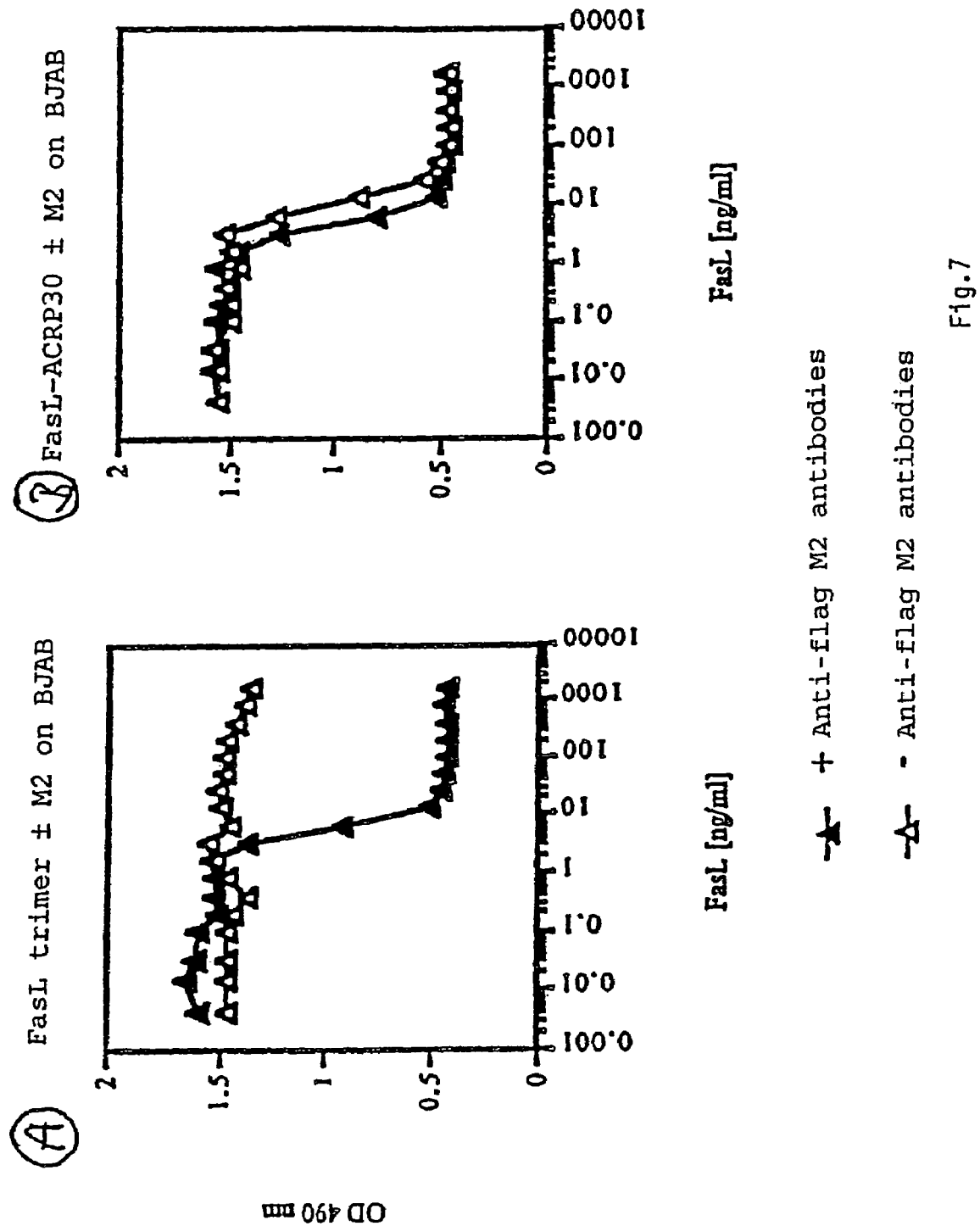

Analogue to FIG. 3, FIG. 7 shows the viability of BJAB cells after the addition of FasL trimers incapable of bimerizing or oligomerizing (comparative experiment on the basis of fusion protein (1) in accordance with FIG. 1; FIG. 7A) and of oligomers in accordance with the present invention, here as tetramers of trimers, in other words dodekamers, of the fusion protein (4) in accordance with the invention and with FIG. 6 in the presence (▲) or absence (Δ) of anti-flag M2 antibodies. Whereas the FasL trimers which are not in accordance with the present invention do not develop an apoptotic effect on the BJAB cells in the absence of antibodies which oligomerize through binding to the flag sequence (FIG. 7A, (Δ)), a dodekamer in accordance with the present invention (tetramer of trimers) of fusion protein (4) induces cell death already at a concentration of approx. 10 ng/ml ($K_{50}$=8 ng/ml) (FIG. 7B). This can be seen quite clearly through a reduction of the OD at 490 nm. This apoptotic activity can be increased slightly through the addition of anti-flag M2 antibodies to a preparation of dodekamers in accordance with the present invention consisting of FasL-ACRP30 fusion proteins in accordance with the present invention, i.e. a dodekamer in accordance with the present invention represents a practically optimum aggregation status with regard to the apoptotic activity. In contrast, the further aggregation to higher order aggregates in accordance with the present invention triggered by corresponding antibodies is not able to bring about any further significant biological effects.

Figure 8:
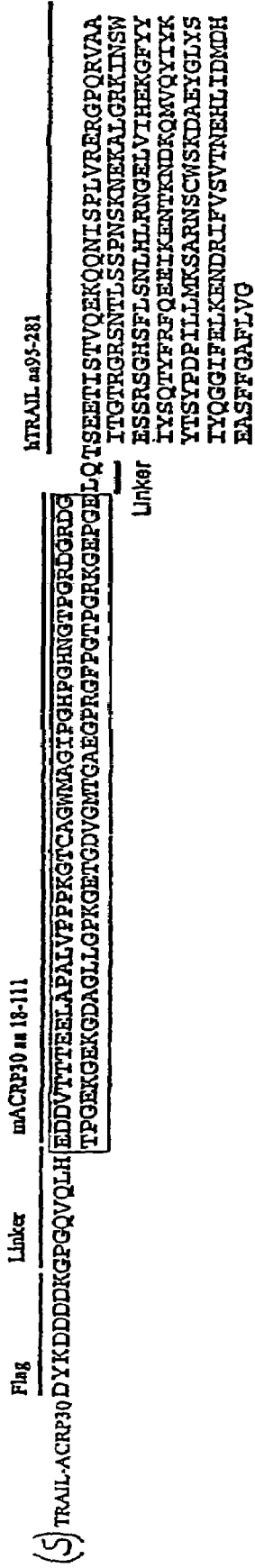

The amino acid sequence of a fusion protein (5) in accordance with the present invention,. which contains amino acids 95 to 281 of hTRAIL as component A in combination with the oligomerizing domain of ACRP30 (AA 18-111) as component B is shown in FIG. 8 (TRAIL-ACRP30; SEQ ID NO:5). In accordance with the present invention, therefore, the fusion protein (5) is found in solution as an oligomer, namely as a tetramer of trimers.

Figure 9:
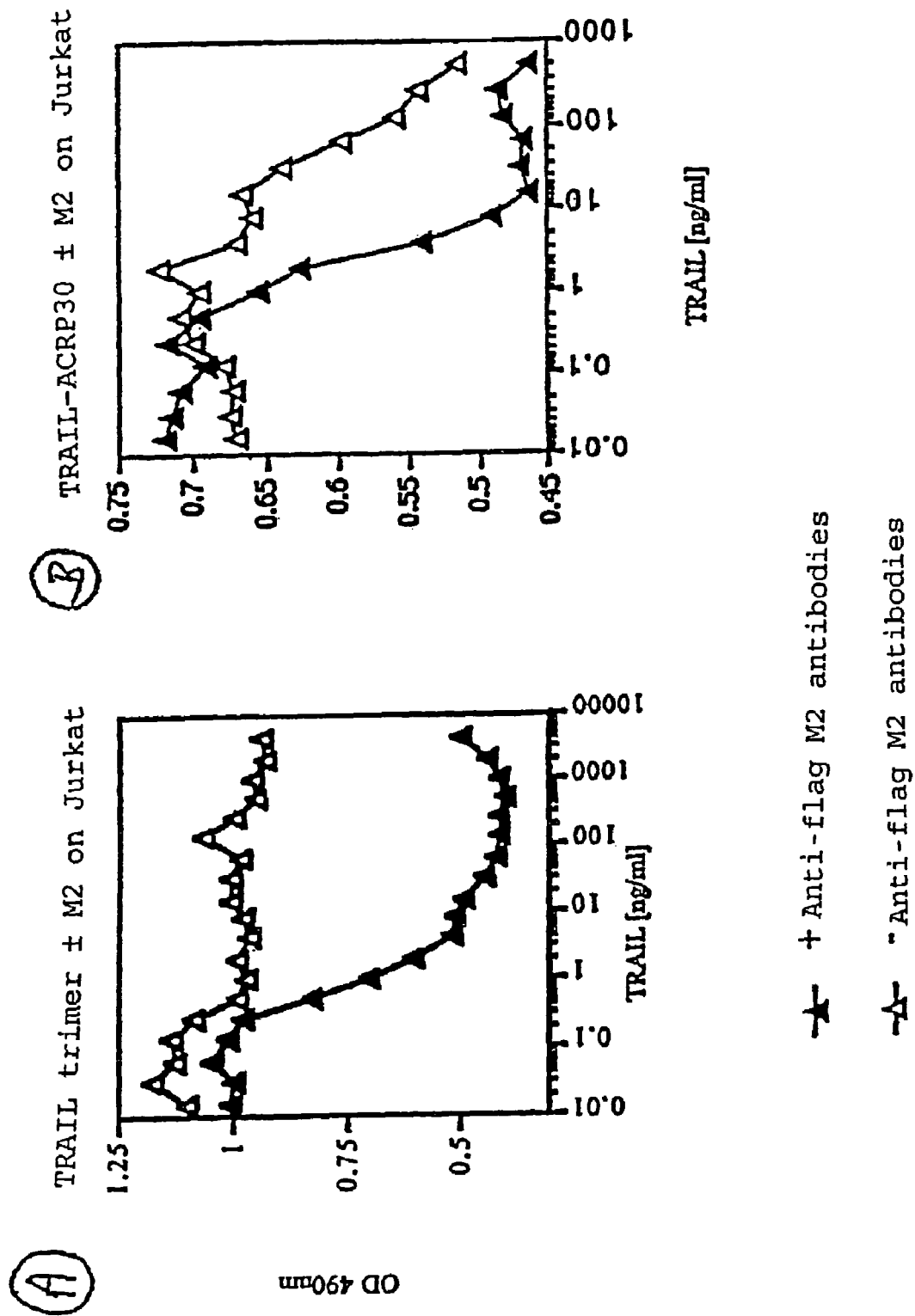

FIG. 9 shows the viability of Jurkat cells after the addition of TRAIL trimers (fusion protein with a flag sequence at the N terminus and the amino acids 95 to 281 of human TRAIL) in accordance with the state of the art without the capability of bimerizing or oligomerizing (comparative experiment, FIG. 9A) and of dodekamers in accordance with the present invention of the fusion protein (5) in accordance with the present invention, TRAIL-ACRP30, in the presence (▲) or absence (Δ) of anti-flag M2 antibodies. The observations in the experiment in FIG. 9 correspond to the findings shown in FIG. 7. Whereas the TRAIL trimers do not develop an apoptotic effect on the Jurkat cells in the absence of antibodies which oligomerize though binding to the flag sequence (FIG. 9A, (Δ)), the dodekamer in accordance with the present invention of fusion protein (5) induces cell death in this experiment as well at a concentration of approx. 100 ng/ml ($\approx K_{50}$) (FIG. 9B (Δ)). By increasing the degree of oligomerization further, the combined addition of TRAIL dodekamers and anti-flag antibodies can in addition form higher order aggregates in accordance with the present invention, which in this case have an increased (at least tenfold) apoptosis-inducing activity (FIG. 9B, (▲)), from oligomers in accordance with the present invention.

Figure 10:
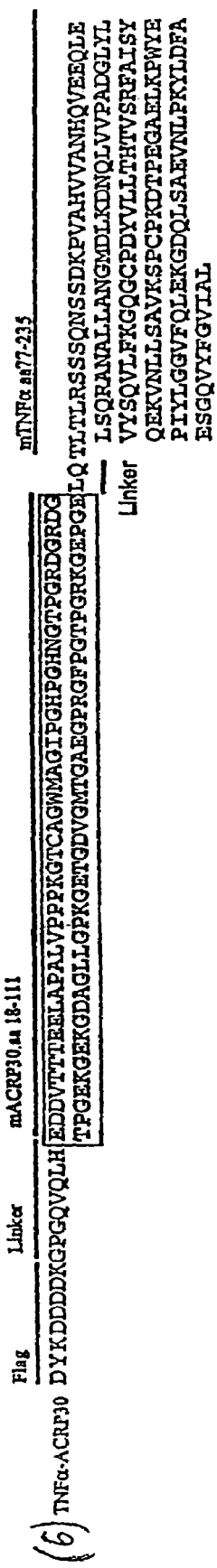

The amino acid sequence of a fusion protein (6) in accordance with the present invention, which contains the amino acids 77 to 235 of mTNFα (m: murine) as component A in combination with the oligomerizing domain of mACRP30 (AA 18-111) as component B and a flag sequence with linker at the N terminus, is shown in FIG. 10 (TNFα-ACRP30: SEQ ID NO:6). This means that the fusion protein (6) is found in solution as a dodekamer, namely as an oligomer (tetramer) of multimers (trimers).

Figure 11:
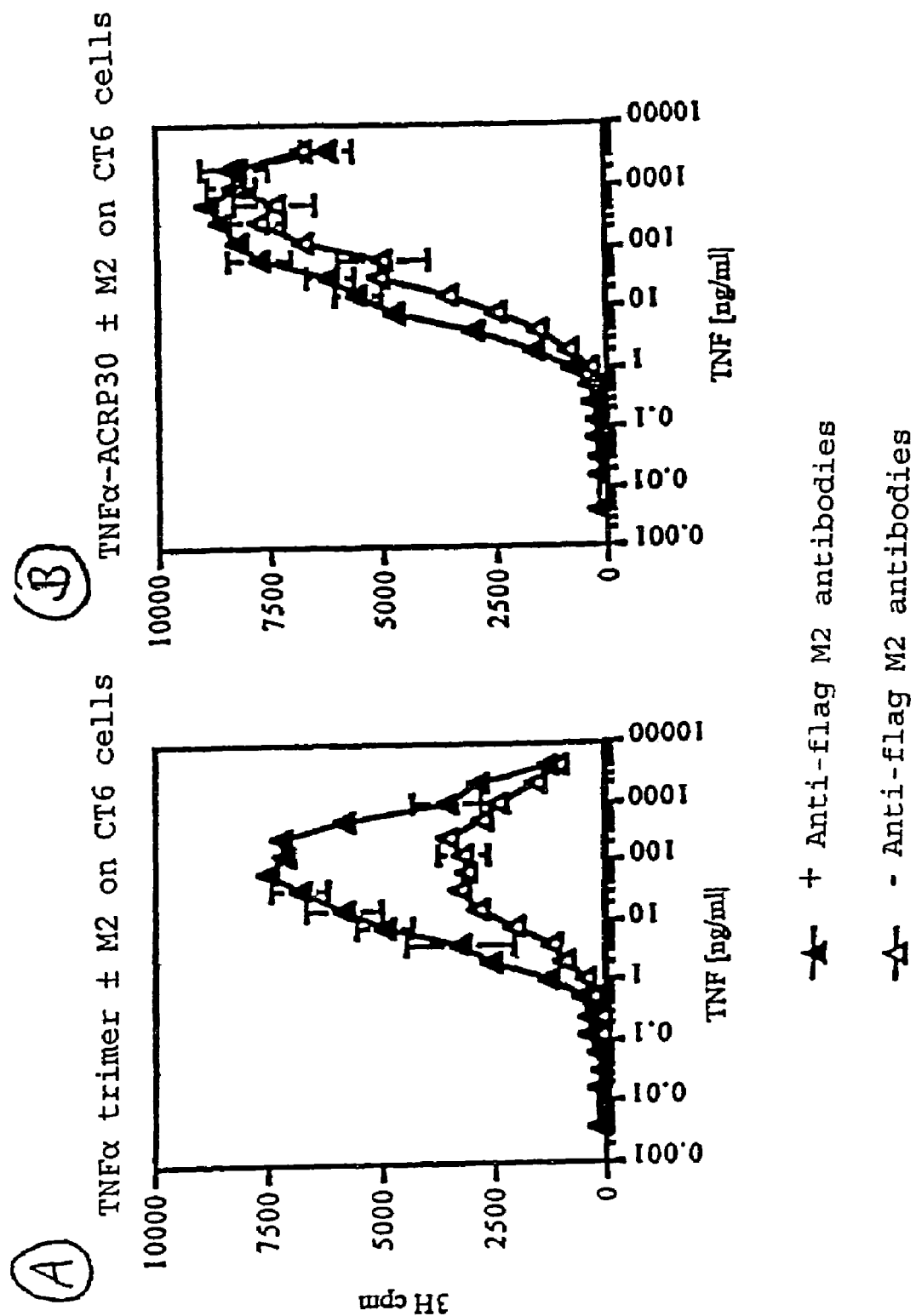

FIG. 11 shows the findings of a cell proliferation experiment. Here as a value for the cell proliferation of CT6 cells the incorporation of $^3$[H]-thymidin into the CT6 cells of mice as a function of the concentration of trimers of a fusion protein in accordance with the state of the art (flag and linker sequence at the N terminus with subsequent amino acids 77 to 235 from murine TNFA) without a component B was determined, in other words of the mTNFα trimer (FIG. 11A), or of dodekamers (4×3) in accordance with the present invention of the fusion protein (6) in accordance with the present invention according to FIG. 6, mTNFα-ACRP30 (FIG. 11B). The incorporation of $^3$ [H]-thymidin is shown in counts-per-minute (cpm). The experiments were carried in the presence (▲) or absence (Δ) of anti-flag M2 antibodies. Here the trimer of mTNFα which is familiar from the state of the art has only a slight proliferating effect on the CT6 cells after binding to the TNF receptor 2 (TNF-R2) (FIG. 11A). A clearly increased proliferating effect can only be observed after the addition of anti-flag antibodies (▲) through their cross-linking and therefore oligomerizing effect.

In contrast to this, in FIG. 11B oligomers in accordance with the present invention of the trimers, here the dodekamer of the fusion protein (6) in accordance with the present invention, show a heavy proliferating effect which can already be observed at 5 ng/ml (Δ). The combination of cross-linking anti-flag antibodies and dodekamers (▲) in accordance with the present invention as reference can in contrast only bring about a slight increase of the proliferating effect in comparison with the findings with the sole addition of the dodekamer in accordance with the present invention. It can be seen from this that an oligomer in accordance with the present invention, here in form of a dodekamer, already has a practically optimum proliferation effect.

The amino acid sequence of a fusion protein (7) in accordance with the present invention, which contains the amino acids 116 to 261 of hCD40L (h: human) as component A in combination with the oligomerizing domain of ACRP30 (AA 18-111) as component B, is shown in FIG. 12 (CD40L-ACRP30; SEQ ID NO:7).

Figure 13:
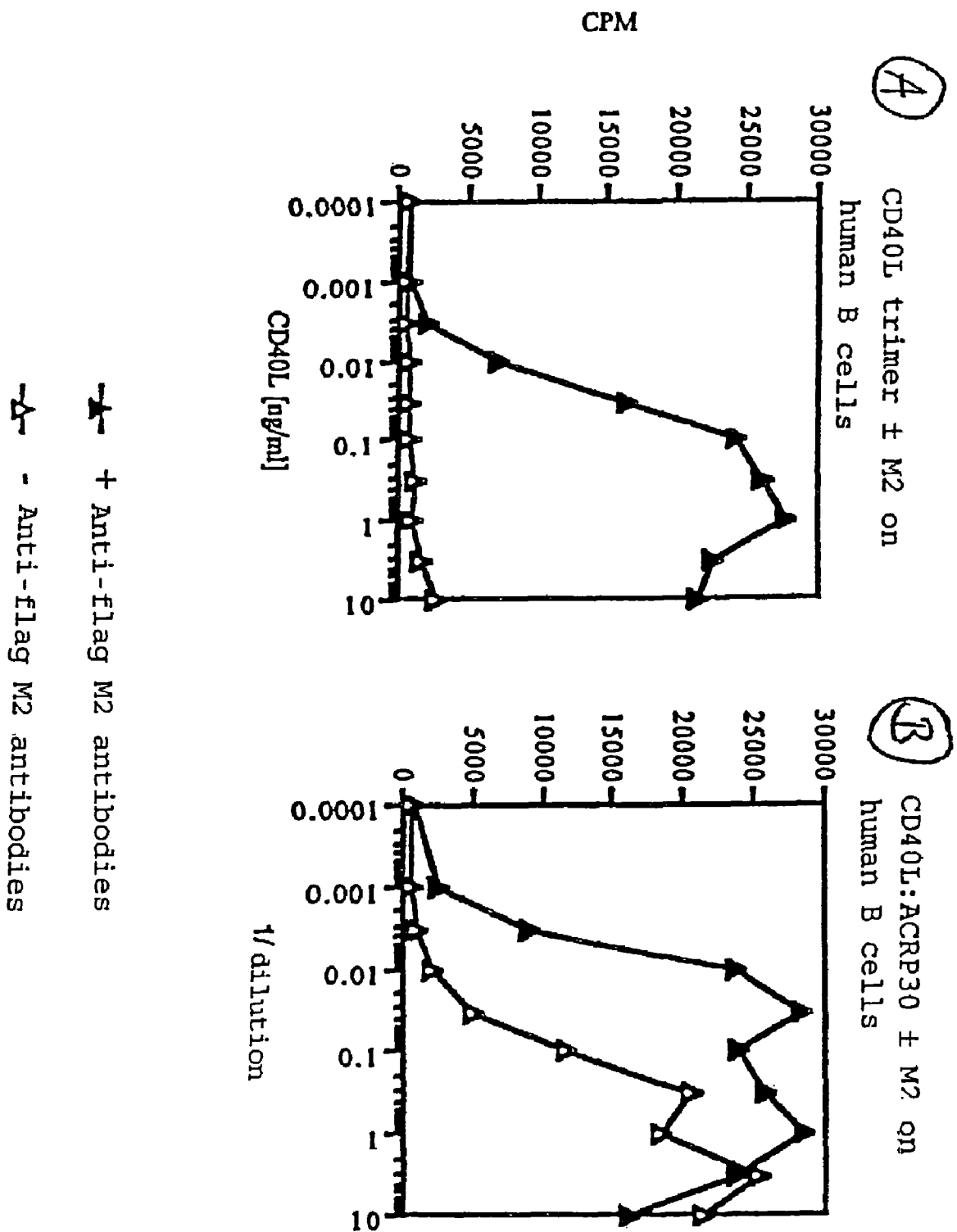

FIG. 13 shows, in exactly the same way as FIG. 11, the findings of a cell proliferation experiment. However, in this case, in contrast to FIG. 11, human PBL (peripheral blood lymphocytes) were used. The figure shows the effect of traditional CD40L, which is present in solution in the form of a trimer (flag and linker sequences, as in FIG. 12, with subsequent sequence from AA 16 to 261 of hCD40L without an oligomerizing component B; FIG. 13A), on the cell proliferation in comparison with the effect of dodekamers in accordance with the present invention of fusion proteins (7) in accordance with the present invention as shown in FIG. 12, CD40L-ACRP30 (FIG. 13B). The experiments carried out in the absence (Δ) of anti-flag M2 antibodies show that the CD40L trimer has practically no proliferating effect, whereas in FIG. 13B a corresponding proliferating effect can already be detected with much lower concentrations of hCD40L. In FIG. 13B, the x-axis shows the variable "1/dilution", in other words, not absolute concentrations, because a concentrated supernatant, whose absolute concentration is unknown, was added. The combination of cross-linking anti-flag antibodies and dodekamers of fusion protein (7) in accordance with the present invention (▲) as reference can generate a further (to lower concentrations) shift of a corresponding proliferation effect through the formation of higher order aggregates.

Figure 14:
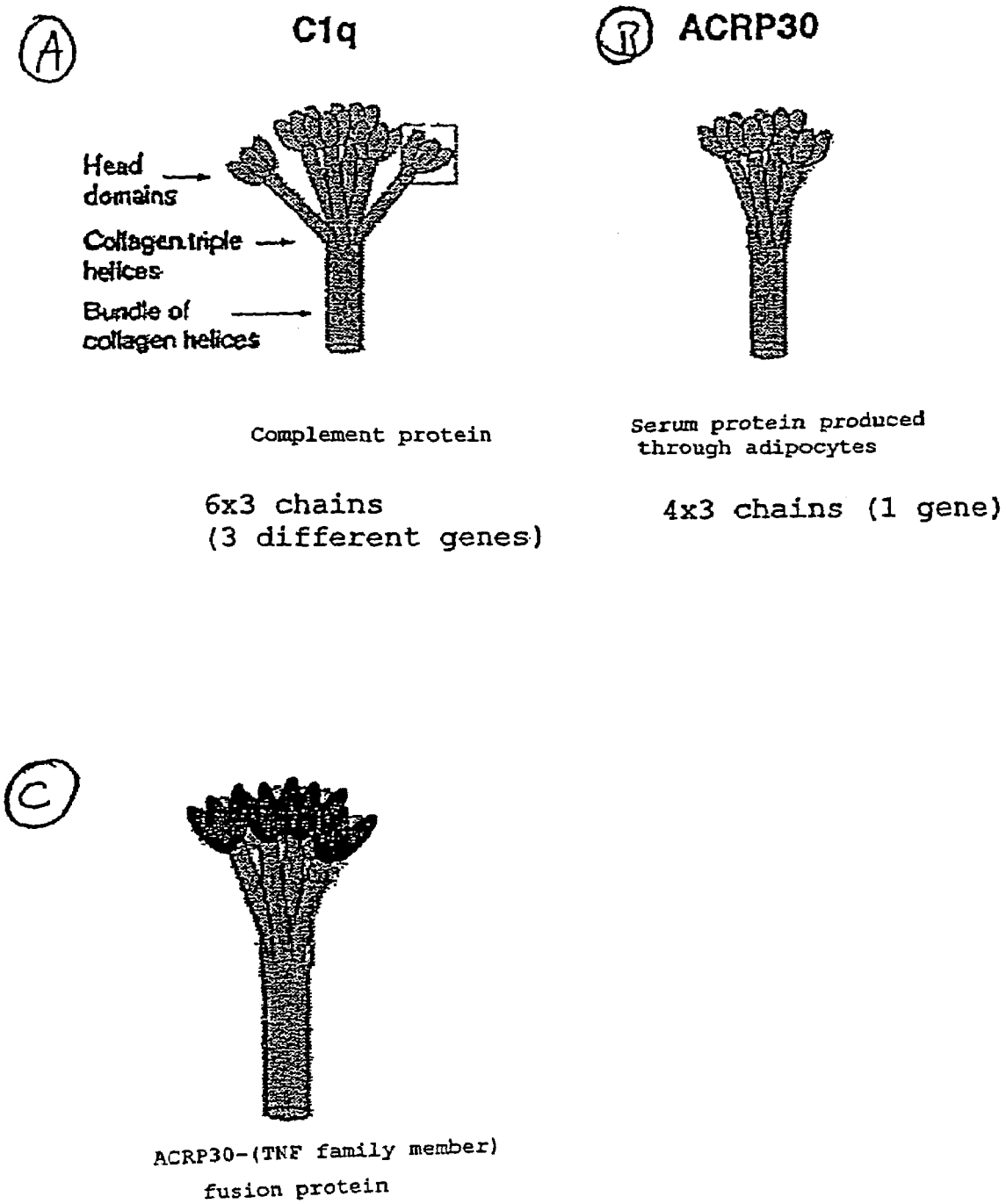

FIG. 14 shows a schematic representation of the structure of oligomerized multimers. FIGS. 14A and 14B show schemas of the appearance of native "bundle proteins" with their already native oligomerized structure (FIG. 14A: hexamer of head domain trimers which form the complement protein C1q; FIG. 14B: tetramer of head domain trimers which form ACRP30, a serum protein produced through adipocytes). In this way, the head domains of the native monomers at the C1q or ACRP30 complex are multimerized and oligomerized. Whereas the C1q oligomerizing complex is formed from three different gene products, the ACRP30 oligomerizing complex is a homododekamer, in other words identical multimerized and oligomerized gene products. The respective individual polypeptide chains on which the above-mentioned native oligomerizing complexes are based each have a head domain, a sequence section which can form a collagen triple helix, and a sequence section which can oligomerize 6 (C1q complex) or 4 (ACRP30 complex) collagen triple helices into a helix bundle of 18 or 12 monomers, respectively.

FIG. 14C contains a schematic representation of a oligomerized multimer in accordance with the present invention of a fusion protein in accordance with the present invention (e.g. fusion protein (4) as shown in FIG. 6, FasL-ACRP30), which has four trimerized TNF ligands (e.g. the TNF ligand FasL) or segments of TNF ligands as component A, which oligomerize to a homododekamer in accordance with the present invention through the collagen-like sequence sections of the ACRP30 protein as component B, which is found, for example, in a fusion protein in accordance with the present invention.

Figure 15A:
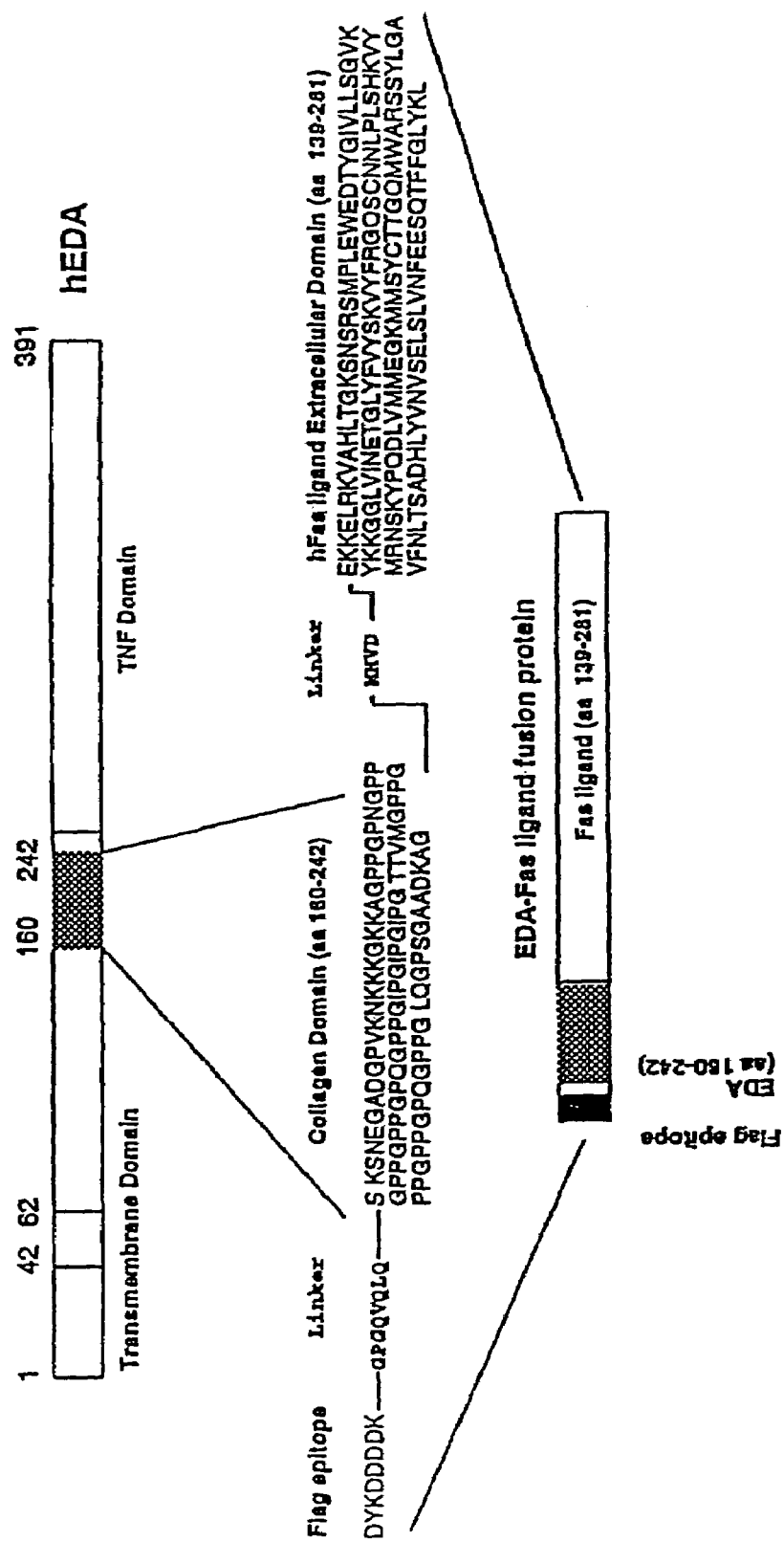

FIG. 15A describes the construction of a further fusion protein according to the present invention, namely hEDA/FasL (SEQ ID NO:9). Herein, the collagen domain of human EDA (amino acids 160 to 242) serves as component B to which a Flag epitope is fused N-terminally via a linker and to which a component A, FasL (AA139-281, i.e. the extracellular domain of FasL or a fragment thereof) in FIG. 15A, is coupled C-terminally also via a linker. The fusion protein hEDA/FasL according to the present invention is present as a hexamer, a 2×3 mer. The EDA protein is a further member of the TNF family, which has also a collagen domain (FIG. 15A above) besides a transmembrane domain and a TNF domain, and comprises 391 AA in its human form.

Figure 15B:
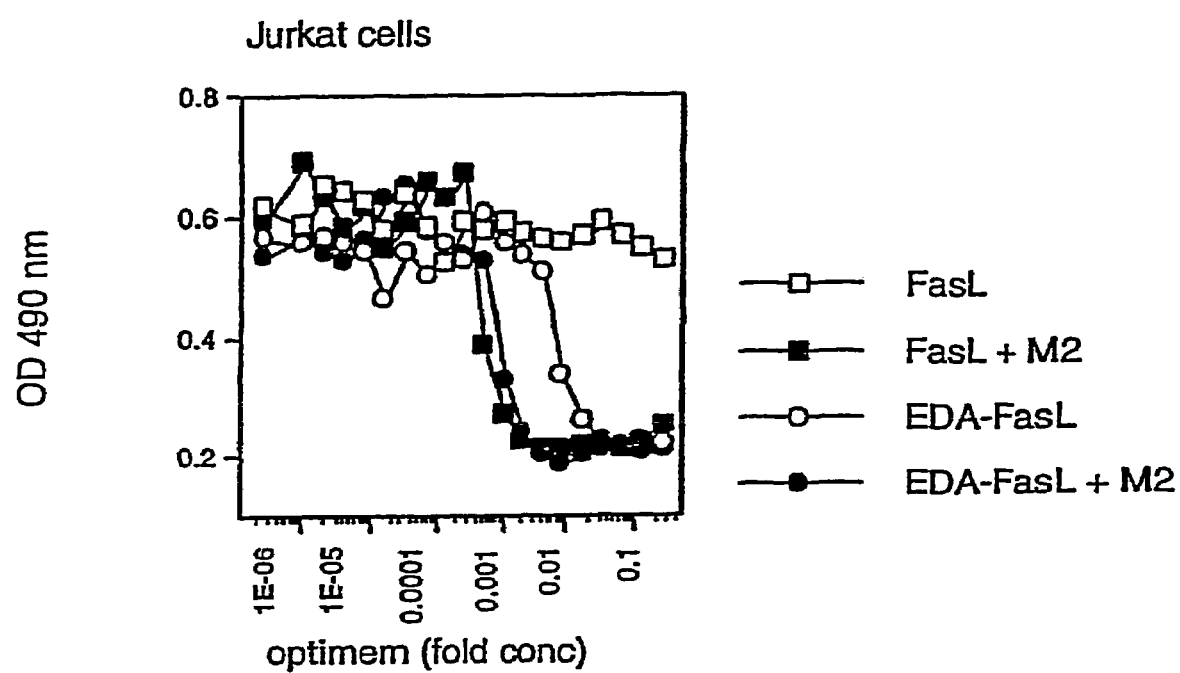

FIG. 15B illustrates studies with the fusion protein hEDA/FasL according to the present invention. For the production of the fusion protein, the collagen domain of human EDA (AA 160 to 242) was initially amplified by corresponding primers and then fused to the corresponding sequences at the N- and C-terminus, respectively, for Flag and the extracellular domain of human FasL (AA 139 to 281). Now, FIG. 15B represents curves resulting from the titration of Jurkat T-cells with FasL on the one hand and the fusion protein hEDA/FasL on the other hand, under addition of anti-Flag antibody M2 and without addition of anti-Flag antibody M2. Supernatants (OPTIMEM) of 293-cells, being transiently transfected with FasL or hEDA/FasL and expressing these proteins, were therefore added to Jurkat T-cells. In successive experiments, the decreasing concentrations shown on the x-axis of FIG. 15B were employed and the respective viability rate of the Jurkat T-cells was determined by the standard cytotoxicity test described elsewhere. From the graph it is clear that FasL is inactive without crosslinking M2 antibody (□), and in this case only the crosslinking effect by the antibody M2 causes cytoxic effects (■). In contrast thereto, the corresponding effect of a fusion protein according to the present invention, namely hEDA/FasL, is already achieved without addition of M2 antibody (○). In this case, the addition of M2 antibodies is still able to increase the effect of the fusion protein according to the present invention (●).

The present invention is explained in more detail by means of the following embodiments:

The following experimental situations (a) to (f) are to be referred to for the six following embodiments, in so far as appropriate and corresponding modifications disclosed loc. cit. do not apply:

(a) Vector Constructions for the FasL, TRAIL, TNFα and CD40L Fusion Proteins

A DNA fragment encoding for the signal peptide of haemaglutinin, including 6 bases of the untranslated sequence in the 5' region (CAA AAC ATG GCT ATC ATC TAC CTC ATC CTC CTG TTC ACC GCT GTG CGG GGC; SEQ ID NO:15) and the flag epitope (GAT TAC AAA GAC GAT GAC GAT AAA; SEQ ID NO:16), the linker (GGA CCC GGA CAG GTG CAG; SEQ ID NO:17), the restriction sites PstI, SalI, XhoI and BamHI were cloned between the restriction sites HindI and BamHI of a modified PCRIII vector (In Vitrogen, NV Leek, Netherlands) in which the bases 720-769 were deleted (PS 038). For the expressions vector of the trimeric FasL the amino acids 139 to 281 of the sequence encoding for human FasL, framed by the restriction sites PstI and EcoRI, were amplified with PCR and cloned in the modified PCRIII vector.

For the hexameric FasL the encoding sequence for the amino acids 103 to 281, framed on both sides by EcoRI restriction sites and in addition at the 5' end by the linker sequence GGCTT and at the 3' end by the stop codon (TAA) and the natural, untranslated sequence (GAG AAG CAC TTT GGG ATT CTT TCC ATT ATG ATT CTT TGT TAC AGG CAC CGA GAT GTT GAA GCC; SEQ ID NO:18) was cloned into the EcoRI restriction site of the vector PS 038. The "super FasL" (FIG. 4, fusion protein (3)) was generated by the introduction of a point mutation in the linker sequence of the vector PS 038, in that the sequence CAGTGTGCTG (SEQ ID NO:19) on the 5' side of the EcoRI restriction site was replaced by CAGTCTGCAG (SEQ ID NO:20) with the help of PCR mutation methods. Following this the FasL (amino acids 103 to 281 was cloned into the modified PS 038 in the manner described above.

For human TRAIL, murine TNFα and human CD40L, parts of the extracellular domains (TRAIL: qamino acids 95 to 281, TNFα: amino acids 77 to 235, CD40L: amino acids 116 to 261) with PstI restriction sites at the 5' end and a stop codon and SpeI and EcoRI restriction sites were amplified through PCR and cloned in the vector PCRII (Invitrogen). For the expression of the ligands as trimer firstly the sequence GAT TAC AAA GAC GAT GAC GAT AAA (SEQ ID NO:16), encoding for the flag tag, and the linker sequence GGA CCC GGA CAG GTG CAG (SEQ ID NO:17) were inserted between the restriction sites BamHI and PstI in the vector pQE-16 (Qiagen) (PS 330). Finally, the ligands were sub-cloned as PstI/SpeI fragments in PS 330.

The expression vector for FasL-ACRP30 was constructed in the following way. By means of the EST clone AA673154, the encoding sequence for the amino acids 18 to 111 of the murine ACRP30, framed by the restriction sites NsiI and PstI, was cloned by PCR methods into the PstI restriction site of the vector encoding for trimeric FasL (in such a way that the fusioned NsiI/PstI restriction site was located on the 5' side of the encoding sequence). The vectors for the expression of the fusion proteins of the other TNF cytokines with ACRP30 were created by substitution of the corresponding sequence of FasL in the expression vector FasL-ACRP30 by the respective ligand sequence into the restriction sites PstI and EcoRI.

(b) Expressing and Purifying the Recombinant Fusion Proteins:

Stable clones were established in bacteria (strain M15 with plasmid pRep4, Qiagen) for the trimeric TRAIL, TNFα and CD40L. The respective clones were precultivated overnight at 37° C. in LB broth with ampicillin (100 μg/ml) and kanamycin (50 μg/ml) and were used to inoculate the main culture (dilution 1:50, growth at 37° C.), which was induced for the expression after one hour with 0.5 mM IPTG (Sigma) for six hours. The bacteria were harvested by means of centrifugation, washed twice in PBS, lysated in the "French press" and the lysate was separated from the insoluble rest by centrifugation. Stable clones were made for all FasL proteins in HEK293 cells by means of selection in 800 μg/ml G418 (see loc. cit. as well: Schneider et al., J. Exp. Med, 1998).

The trimeric and hexameric ligands and super FasL were purified from the supernatants of stable clones or of bacterial lysates by means of affinity chromatography on M2 agarose (Sigma, Switzerland), eluted with 50 mM citrate NaOH (pH=2.5) and immediately neutralized with 0.2 volume Tris-HCl (pH=8). The buffer was replaced by PBS in concentrators (Centrikon-30, Amicon Corp., Easton, Tex., USA).

Fusions of FasL with murine ACRP30 were purified in the following manner. The supernatants were mixed with 50 mM NaCl and 1 mM $CaCl_2$ and the pH value was set to 7.0 by means of hydrochloric acid/NaOH. The recombinant protein was then bound to M1-agarose (Sigma, Switzerland) and eluted in TBS-EDTA (10 mM). The buffer was replaced by PBS in concentrators. The concentration of purified proteins was determined through the bicinchonin acid process (Pierce Chemical Co., Rockford, Ill., USA) using bovine serum albumin as a standard and the purity of the samples was determined through SDS-PAGE and Coomassie Blue staining.

The fusion proteins of TRAIL, TNFα and CD40L with ACRP30 were added in the respective assays in the form of enriched supernatants which were produced in the following manner: 293T cells were transfected with the respective expressions plasmids through the calcium phosphate method. After the cells had been incubated with the precipitate for 16 hours, the cells were washed with PBS and incubated for 4 days in a serum-free medium (Optimen, Gibco BRL). The supernatants were reduced to one-twentieth of the original volume through concentrators and the presence of the protein was checked with Western blotting. In the case of TRAIL-ACRP30 and TNFα-ACRP30 titrations of these proteins were compared with titrations of purified trimeric TRAIL or TNFα in order to determine the respective concentration of the recombinant fusion proteins.

(c) Checking the Molecular Weight of the Multimers Through Gel-permeation Chromatography:

The size of the different fusion proteins was determined through gel-filtration on Superdex 200 HR10/30 (Pharmacia). Recombinant protein with the internal standards catalase and ovalbumin in the case of the trimeric and hexameric ligands, and ferritin and ovalbumin for the ACRP30 fusion proteins, was loaded onto the column in a volume of 200 μl, eluted with PBS (0.5 ml/min) and collected in fractions of 0.25 ml. The presence of the proteins in the different fractions after precipitation through trichloro ethanoic acid was determined with Western blotting. The size of the proteins was determined with the help of thyroglobulin (669 kDa), ferritin (440 kDa), catalase (262 kDa), aldolase (158 kDa), bovine serum albumin (67 kDa), ovalbumin (43 kDa) chymotrypsinogen A (25 kDa) and ribonuclease A (13.7 kDa).

(d) Cells:

Murine B-lymphoma. A20 cells were held in DMEM which contained 5% heat-inactivated FCS. The human T-lymphoplastom-Jurkat cells, BJAB Burkitt's-lymphoma cells were cultivated in RPMI, accompanied by 10% FCS. The human embryonic renal cells 293 were cultivated in a DMEM multi-material mixture F12 (1:1), accompanied by 2% FCS. All media contained antibiotics (penicillin and streptomycin at 5 μg/ml respectively and neomycin at 10 μg/ml). The IL-2 dependent murine cytoxic T-cell line CT6 was cultivated in RPMI, supplemented by 10% FCS, 1 mM natriumpyruvate, 50 μM 2-mercaptoethanol, 10 mM hepes and 10% conditioned EL-4 cell supernatant.

(e) Cytotoxic Assay:

The cytotoxic assay was carried out essentially as described previously by Schneider et al. (J. Biol. Chem., 272:18827-18833, 1997). Fifty thousand cells were incubated for a period of 16 hours in 100 μl medium, whereby the medium contained the displayed ligand concentrations in the presence or absence of 1 μg/ml M2 antibody (2 μg/ml for TRAIL). The viability (cell survival rates) were determined with the help of PMS/MTS (phenanzinmethosulphate 3-[4, 5-dimethylthiazol-2-yl]-5-[3-carboxymethoxyphenyl]-2-[4-sulfophenyl]-2H-tetrazolium, salt] (Promega Corp., Madison, Wis.). The colour development was allowed for the required time (typically 1-3 hours). The absorbance was measured at 490 nm.

(f) B Cell Proliferation Assay:

CD19 positive cells were selected by means of FACS sorting from human PBL (peripheral blood lymphocytes) with magnetic "beads" and purified, whereas CD-19 negative cells were irradiated with 3000 rad. One hundred thousand purified CD-19 positive cells were incubated for 72 hours in 96-well plates with 100,000 autologous CD-19 negative irradiated PBL in 120 μl medium (RPMI 10% FCS, antibiotics) with the titrated soluble CD40L fusion proteins, with or without M2 antibodies (10 μg/ml). Subsequently, the cells were pulsed for 6 hours with [³H]-thymidin and the incorporation was measured with liquid scintillation counting.

With regard to the description of the methods used for implementing the embodiments explicit reference is made otherwise to Schneider et al. (J. Exp. Med., Vol. 187, No. 8, 1998, 1205-1213) and the publications quoted there as references.

1st EMBODIMENT

A recombinant fusion protein (2) was expressed which had the amino acids 103 to 281 of the hFasL (h: human) as component A and at the N-terminus of amino acid 103 a sequence of 18 AA (VDLEGSTSNGRQCAGIRL, so-called specific linker) as component B. In addition, a flag sequence with the amino acids DYKDDDDK and a linker sequence GPGQVQLQ following this was coupled at the N-terminus of the fusion protein (N-terminal of component B)(FIG. 1).

For comparative experiments, a fusion protein (1) was expressed which also had the above-mentioned flag sequence at the N-terminus with the same linker sequence following at the C-terminus and connected to this at the C-terminus the amino acids 139 to 281 of hFasL. Accordingly, fusion protein (1) differs from fusion protein (2) through a deletion which covers the specific linker and the amino acids 103 to 138 of hFasL (FIG. 1).

The vector construction of the fusion proteins (1) and (2) took place in accordance with the procedure described in (a). The expression and purification of the fusion proteins took place in accordance with the procedure described in (b).

The purified fusion proteins (1) were subjected to reducing or non-reducing conditions and then gel electrophoretically separated (FIG. 2), linked with a rough determination of the molecular weight of the respective bands.

Finally, A20 and Jurkat cells cultivated in accordance with (d) were removed and subjected to a cytotoxic assay in accordance with (e). The assay was carried out (FIG. 3) for each of the two cell lines with increasing concentrations of trimerized fusion protein (1) or of bimers of trimers (in other words hexamers) of the fusion protein (2) in the presence or absence of anti-flag M2 antibodies (Sigma, Buchs, Switzerland), in that the absorbance was determined at OD 490 mm.

2nd EMBODIMENT

A recombinant fusion protein (3) was expressed which had the amino acids 103 to 281 of the hFasL as component A and at the N-terminus of amino acid 103 a sequence of 18 AA (VDLEGSTSNGRQSAGIRL (SEQ ID NO:10), so-called specific linker), as component B. In addition, a flag sequence with the amino acids DYKDDDDK (SEQ ID NO:12) and a linker sequence GPGQVQLQ (SEQ ID NO:13) following this was coupled at the N-terminus of the fusion protein (N-terminally from component B), (FIG. 4) For comparative experiments the fusion protein (1) was expressed in the same way as the 1st embodiment (FIG. 4).

The vector construction of the fusion proteins (3) and (1) took place in accordance with the procedure described for embodiment 1. The expression and purification of the fusion proteins took place in accordance with the procedure described in (b).

Finally, A20 and Jurkat cells cultivated in accordance with (d) were removed and subjected to a cytotoxic assay in accordance with (e). The assay was carried out (FIG. 5) for each of the two cell lines with increasing concentrations of trimerized fusion protein (3) in the presence or absence of anti-flag M2 antibodies (Sigma, Buchs, Switzerland), in that the absorbance was determined at OD 490 mm.

3rd EMBODIMENT

A recombinant fusion protein (4) was expressed which had the amino acids 139 to 281 of the hFasL as component A and at the N-terminus of amino acid 139 of component A firstly the linker dimer with the sequence LQ and then still further N-terminally a sequence of 94 AA from the protein mACRP30 (AA 18 to 111), the oligomerizing domain, as component B. In addition, a flag sequence with the amino acids DYKDDDDK (SEQ ID NO:12) and a linker sequence GPGQVQLH (SEQ ID NO:21) following this was coupled at the N-terminus of the fusion protein (4) N-terminally from component B) (FIG. 6).

The fusion protein (1) was used for comparative experiments.

The expression and purification of the fusion proteins took place in accordance with the procedure described in (b).

Finally, BJAB Burkitt's lymphoma cells and Jurkat cells cultivated in accordance with (d) were removed and subjected to a cytotoxic assay in accordance with (e). The assay was carried out (FIG. 7) for each of the two cell lines with increasing concentrations of trimers of the fusion protein (1) or of oligomerized trimers (dodekamers) of fusion protein (4), that means of the recombinant FasL-ACRP30 (4×3), in the presence or absence of anti-flag M2 antibodies (Sigma, see above), in that the absorbance was determined at OD 490 mm.

4th EMBODIMENT

A recombinant fusion protein (5) was expressed which had the amino acids 95 to 281 of the hTRAIL (h: human) as component A and at the N-terminus of amino acid 95 of component A firstly the linker dimer with the sequence LQ and then more N-terminally a sequence of 94 AA from the protein mACRP30 (AA 18 to 111), the oligomerizing domain, as component B. In addition, a flag sequence with the amino acids DYKDDDDK and a linker sequence GPGQVQLH following this was coupled at the N-terminus of the fusion protein (N-terminally from component B)(FIG. 8).

For comparative experiments a fusion protein was expressed (not shown in FIG. 8; SEQ ID NO:5) which is found in solution as a trimer (TRAIL trimer). This comparative experiment protein has (from the N-terminus to the C-terminus) the flag sequence, the linker with the sequence GPGQVQLH (SEQ ID. NO:21) and finally hTRAIL (AA 95 to 281). In contrast to fusion protein (5) the component B (mACRP30: AA 18 to 111) and the linker with the sequence LQ are missing.

The expression and purification of the fusion proteins took place in accordance with the procedure described in (b).

Finally, T-lymphoblastoma Jurkat cells cultivated in accordance with (d) were removed and subjected to a cytotoxic assay in accordance with (e). The assay was carried out (FIG. 9) with increasing concentrations of trimers of the fusion protein without the ACRP30 sequence (for a comparison) or of the oligomerized trimers of the fusion protein (5), in other words of a dodekamer of the recombinant TRAIL-ACRP30 (4×3), in the presence or absence of anti-flag M2 antibodies (Sigma, see above), in that the absorbance was determined at OD 490 mm.

5th EMBODIMENT

A recombinant fusion protein (6) was expressed which had the amino acids 77 to 235 of the mTNFα (m: murine) as component A and at the N-terminus of amino acid 85 firstly the linker dimer with the sequence LQ and then further N-terminally a sequence of 94 AA from the protein mACRP30 (AA 18 to 111), the oligomerizing domain, as component B. In addition, a flag sequence with the amino acids DYKDDDDK (SEQ ID NO:12) and a linker sequence GPGQVQLH (SEQ ID NO:21) following this was coupled at the N-terminus of the fusion protein (N-terminally from component B) (FIG. 10).

For comparative experiments a fusion protein was expressed (not shown in FIG. 10) which is found in solution as a trimer (TNFα trimer). This comparative experiment protein has (from the N-terminus to the C-terminus) the flag sequence, the linker with the sequence GPGQVQLH and finally mTNFα (AA 77 to 235). In contrast to fusion protein (6) the component B (mACRP30: AA 18 to 111) and the linker with the sequence LQ are missing.

The expression and purification of the fusion proteins took place in accordance with the procedure described in (b).

With the help of a cell proliferation assay in accordance with (f) the effects of adding increasing concentrations of TNFα trimers or TNFα-ACRP30 oligomers (homododekamers of TNFα) in the presence or absence of anti-flag M2 antibodies (Sigma, see above) to CT6 cells were determined.

For this purpose, CT6 cells were prepared for a period of 4 days before the proliferation experiment in the presence of reduced concentrations of EL-4 supernatants (2.5%). The cells were incubated in 96-well titre plates (40,000 cells per well) for a period of 16 hours with the indicated concentrations of TNFα-ACRP30 oligomers or mTNFα in the presence or in the absence of 2 µg/ml M2 monoclonal antibodies and in the absence of EL-4 supernatant. The cells were pulsed for an additional period of 6 hours with $^3$[H]-thymidin (0.5 µCi/well), subjected to three cycles of freezing and thawing and finally harvested. The $^3$[H]-thymidin incorporation was finally checked by means of a liquid scintillation method (FIG. 11).

6th EMBODIMENT

A recombinant fusion protein (7) was expressed which had the amino acids 116 to 261 of the hCD40L (h: human) as component A and at the N-terminus of amino acid 95 of component A firstly the linker dimer LQ and then further N-terminally a sequence of 94 AA from the protein mACRP30 (AA 18 to 111), the oligomerizing domain, as component B. In addition, a flag sequence with the amino acids DYKDDDDK (SEQ ID NO:12) and a linker sequence GPGQVQLH (SEQ ID NO:21) following this was coupled at the N-terminus of the fusion protein (N-terminally from component B) (FIG. 12).

For comparative experiments a fusion protein was expressed (not shown in FIG. 12) which is found in solution as a trimer (CD40L trimer). This comparative experiment protein has (from the N-terminus to the C-terminus) the flag sequence, the linker with the sequence GPGQVQLH (SEQ ID NO:21) and finally hCD40L (AA 116 to 261). In contrast to fusion protein (7) the component B (mACRP30: AA 18 to 111) and the linker with the sequence LQ are missing.

The expression and purification of the fusion proteins took place in accordance with the procedure described in (b).

Finally, the cell proliferation assay in accordance with (f) was carried out analogously on PBL, whereby CD40L trimer or CD40L-ACRP30 oligomers (homododekamers) were added in the presence or absence of anti-flag M2 antibodies (Sigma, see above) (FIG. 13).

7th EMBODIMENT

7.1 Experimental Procedures

The 7th embodiment refers to fusion proteins which consists of a multimerizing and oligomerizing component A and a receptor as component B.

(A) Vector Constructions

The fusion proteins were constructed from a modified PCR-3 Vector (from Invitrogen) as an arrangement of interchangeable modules in the following order (5' to 3'):

(a) a HindIII/SalI modul, containing the extracellular domain of receptor, with a preceeding Kozak sequence GCCACC (in the case of hTNF-R1 (amino acids 1-211); h-TRAIL-R1 (amino acids 1-239); h-TRAIL-R2 (amino acids 1-212); h-TRAIL-R3 (amino acids 1-240) and hCD40 (amino acids 1-193) or in the case of hFasR (amino acids 1-170) by placing in front 24 nucleotides of the 5'-untranslated region); (b) a 14 amino acid-long linker (PQPQPK-PQPKPEPE; SEQ ID NO:24) within a SalI/XhoI-cassette (as described in Terskikh et al. (1997), Proc. Nati. Acad. Sci. USA 94, 1663); (c) an oligomerization domain in an XhoI/NotI-module in the case of OPG (amino acids 187-401, herein designated as δN-OPG), CMP (amino acids 451-493), GenBank 115555); COMP (amino acids 32-75, GenBank 1705995); (d) a NotI/XbaI-cassette, containing a combined His$_6$-myc-tag and a stop codon. The oligomerization domain was framed by the amino acid sequences GGCC (SEQ ID NO:22) and ARTPGGGS (SEQ ID NO:23) at the N- and C-termini, respectively. Linkers were used for all constructs. In the case of Fc-constructs the "hinge" region, the CH2 and CH3 domains and the stopcodon of hIgGi were cloned as SalI/NotI-cassette as described before (Schneider et al. (1997) J. Biol. Chem. 272, 18827; Schneider et al. (1998) J. Exp. Med. 187, 1205). Stable HEK-293 derived cell lines for the production of recombinant proteins were established by selection in 800 µg/ml G418 by the method described previously (Schneider et al. (1997), bc. cit.).

(B) Transient Transfection 293T cells were transfected by the CaCl$_2$ method as described before (Schneider et al. 1997 loc. cit.) and washed with PBS before they were incubated in serum-free Optimem medium for 3 days. Supernatants were concentrated 30 fold and maintained frozen until needed. The concentration of Fas/δN-OPG and Fas/CMP fusion proteins in concentrated Optimem medium was determined by a titration on "western blots" with the aid of purified Fas/COMP as standard.

(C) Purification of Recombinant Proteins

Supernatants of stably transfected 293-cells were loaded on M2-agarose (as ligand) or protein A-sepharose (Fc fusion proteins), washed with PBS and eluted by 50 mM citrate-NaOH (pH 2,5). The eluate was neutralized by Tris-HCl (pH 8) and the buffer was changed to PBS in centrikon30 concentrators (from Amicon, Easton, Tex.). COMP and CMP fusion proteins were purified on HiTrap-chelate columns. For this purpose, supernatants of stably transfected 293 cells were supplemented by 500 mM NaCl and 10 mM imidazol, and given on columns which were coated with 0,5 M ZnSO$_4$ (pH 2,5), and equilibrated in PBS. The column was washed with PBS and the proteins were eluted with PBS containing 50 mM EDTA. The buffer was changed to PBS as described before.

Flag-FasL and Flag-TRAIL were produced as described before (Schneider et al., 1997, J. Biol. Chem. 272, 18827, and Thome et al., 1997, Nature 386, 517). Both references are included in the disclosure of the subject-matter of the present application by reference. Flag-CD40L (AA 116 to 261) was expressed in bacteria and purified on M2-agarose, as described for Flag-TRAIL. Protein concentrations were determined by the bicinchonic acid method. The degree of purification was examined by SDS-PAGE and Coomassie-Blue staining.

(D) Gel Permeation Chromatography

For gel permeation chromatography, the respective amount of fusion protein in a volume of 200 µl was loaded on to a Superdex 200 HR 10/30 column (from Pharmacia) and eluted in PBS by 0.5 ml/min, concomitantly measuring the absorbance at 280 nm. As described below, the individual fractions (0.25 ml) were analysed in cytotoxicity tests. For the determination of the molecular weight, the column was calibrated with the standard proteins thyroglobulin (669 kD), ferritin (440 kD), catalase (262 kD), aldolase (158 kD), bovine serum albumin (67 kD), chicken ovalbumin (43 kD), chymotrypsinogen A (25 kD) and ribonuclease A (13,7 kD).

(E) Competitive ELISA

The competitive ELISA was carried out as follows. 96 "well"-ELISA-plates were coated with receptor/Fc-fusion protein (0.2 µg/ml in PBS, 100 µl, 16 hours, 25° C.). The wells were saturated for one hour at 37° C. in PBS, the PBS containing 5% fetal calf serum (as blocking buffer). For the use of sCD40L the blocking buffer was PBS, containing 4% fat free milk and 0.05% tween 20. Competing Fc or COMP fusion proteins were serially dissolved in 100 µl blocking buffer in the presence or absence of 1 µg/ml protein A. The ligands were added at a constant concentration (sFasL: 2 µg/ml, 36 nM, sTNFα: 0,02 µg/ml, 0,36 nM; sTRAIL: 0.1 µg/ml 1,4 nM; sCD40L: 0.5 µg/ml, 9.2 nM all in blocking buffer) and were allowed to bind for a period of one hour at 37° C. Bound ligands were identified with an M2-anti-Flagantibody (1 µg/ml in blocking buffer, 100 µl, 45 minutes, 37° C.), peroxidase-conjugated goat-anti-mouseantibody, 1:2000 in blocking buffer, 100 µl, 30 minutes, 37° C.) and o-phenylenediamine hydrochlorid (0.3 mg/ml in 50 mM citric acid, 100 mM $Na_2HPO_4$, 0.01% $H_2O_2$). The absorbance was measured at 490 nm.

(F) Cytotoxicity Tests

The cytotoxicity tests were carried out in 96-well plates in a volume of 100 µl, substantially as described in Schneider et al. (1997), loc. cit. The chimeric receptors were serially diluted in a medium containing amounts of cytotoxic ligands, which were able to induce more than 95% of cell death. Where indicated, protein A was used at a concentration of 1 µg/ml. sFasL was used in the presence of 1 µg/ml M2 and sTRAIL in the presence of 2 µg/ml M2. No M2-antibody was used in the test series with sTNFα. The cells were exposed to a 16 hour incubation, and their viability rates were measured by the use of the PMS/MTS-test systems (phenacinemethosulfate/3-[4,5-dimethylthiazole-2-yl]-5-[3-carboxymethoxyphenyl]-2-[4-sulfophenyl]-2H-tetrazolium, in form of a salt) (Promega, Madison, Wis.). The absorbance was measured at 490 nm. In order to indicate the molar concentrations of the various fusion proteins, the molecular weight was estimated as follows: [(theoretical $M_r$+3 kDa per predicated N-coupled glyan)× multiplicity]. Fas:Fc, :COMP, :CMP, :δN-OPG: 98, 172, 100 and 105 kDa, respectively. TRAILR2:Fc, :COMP:, :CMP, : δN-OPG: 86, 142, 82 and 93 kDa. TNFR1:Fc, :COMP: 104 and 187 kDA. CD40:Fc, :COMP: 101 and 180 kDa. TRAILR2:Fc: 86 kDA, TRAILR3:Fc: 127 kDA. Flag-TRAIL, Flag-FasL, Flag-TNFα, Flag-CD40L: 71, 55, 56 and 54 kDa, respectively.

(G) BIAcore Measurements

The biacore measurements were carried out on CM5-carboxymethyldextran-modified sensor chips (from BIA-core AB, Uppsala, Sweden) at a flow rate of 5 µl/min. The CM5-chips were activated by a 50 µl dose of a 1:1 mixture of N-ethyl-N'-(3-dimethylaminopropyl)-carbodiimide:N-hydroxysuccinimide. Then, six µl of a 100 µg/ml solution of M2-anti-Flag monoclonal antibody in 10 mM $NaHCO_3$ (pH 5,5) were delivered over the activated surface. A 50 µl dose of 1M ethanolamine-HCl deactivated the remaining N-hydroxysuccinimidester. The amount of immobilised M2-antibody, which as needed for the procedure, was about 4600 units. For the analysis of interactions of FasL-Fas:fusion protein and TRAIL-TRAIL-R2: fusion protein, a constant amount of labelled ligand was immobilised on an M2-modified surface. In order to achieve this, a 7 µl dose of 2.5 µg/ml Flag-FasL or Flag-TRAIL was brought on the surface. This led to the binding of about 100 to 150 units. Besides, these conditions allowed a minimal dissociation of the ligands from the M2 surface, as they concomitantly allowed a sufficient subsequent receptor binding for the analysis. The binding of the receptor:fusion protein was then analysed by a 15 µl injection of purified receptor:fusion protein at concentrations between 1 and 100 µg/ml, corresponding to 100 to 150 units. The association kinetics were measured for a period of 3 minutes and the dissociations kinetics for a period of 3 to 5 minutes. Then, the surface was regenerated (to a simple M2 surface) by a 5 µl dose of 50 mM citrate-HCl (pH 2,5). Up to 30 successive repeats of binding and regeneration were carried out without a significant change in the binding characteristics of immobilised M2-antibody. The dissociation and association kinetics were analysed with the aid of the kinetic analysis program provided by the manufacturer using the models AB=A+B and A+B=AB.

(H) Cultivation of Primary Mice Hepatocytes

For the cultiviation of primary mice hepatocytes, C57BL/6 mice were sacrificed, and the liver region above the biliary vessel was removed immediately, in order to then maintain it in a "hepatocyte-attachment medium" (HAM). Initially, the liver region was perfused with 16 ml of 10 mM Hepes (pH 7,6) in order to remove erythrocytes, then with 12 ml of 0.5 mg/ml collagenase H (from Boehringer Mannheim) in Hepes (4 mM $CaCl_2$), and then homogenised in Hepes in a Petri dish. The cells were washed in Hepes, then centrifuged (100×g, 30 seconds) and resuspended in 60% isotonic Percoll solution (from Pharmacia) in HAM, and again centrifuged (700×g, 2 min). All buffers and the medium were used at 37° C. The sedimented cells were resuspended in HAM, counted, seeded on flatdish-formed microtiterplates (10000 per well, 200 µl) and were allowed to attach correspondingly. The experimental mixture (serially diluted inhibitors, sFasL (final concentration: 400 ng/ml, 7 nM) and M2-antibody (final concentration: 1 µg/ml)) were added, and then the cells were incubated for further 16 hours. The Supernatant was removed, fresh HAM (100 µl) was added and the viability test PMS/MTS was carried out as described above.

(I) Activation-induced Cell Death

Flatdish formed microtiter plates were coated with anti-human CD3 TR66 (10 µg/ml) in PBS for a period of 3 hours at 37° C. The plates were washed twice in PBS and once with RPMI 1640 medium. Jurkat cells ($5 \times 10^5$ cells per ml, 100 µl) were mixed with the inhibitors and distributed over each well, then centrifuged (200×g, 3 min), and incubated for a period of 24 hours at 37° C. The viability of the cells (at OD 490 nm) was measured as described above. The specific cell protection (in %) was calculated as follows: [(anti-CD3+inhibitor)−anti-CD3)]/[(control)−(anti-CD3)]× 100.

For providing a mixed-leukocyte culture, splenocytes from perforin-deficient or gld C57BL/6 mice ($H-2^b$) were cultured with gamma-irradiated (36 Gy) splenocytes from Balb/c-mice ($H-2^d$) for a period of 5 days. Before use, non-viable cells were removed from the samples by gradient centrifugation on Ficoll-paque (from Pharmacia Biotech). The labelling was carried out according to the methods described herein-above (Kataoka et. al.). Briefly, target cells (A20 cells) were labelled with natrium [$^{51}$Cr] (from Dupont, Boston, Mass.) for a period of 1 hour, then washed three times with RPMI 1640. MLC cells were mixed with the target cells ($10^4$ cells per well) in U-shaped microtiter plates in the presence or absence of Fas:Fc and Fas:COMP at 40 µg/ml in a final volume of 200 µl and the plates were centrifuged (200×g, 3 min.). After an incubation of 4 hours, the Supernatants were removed and the radioactivity thereof was measured. The specific [$^{51}$Cr]release (in %) was determined by the following formula: [(experimental release−spontaneous release)/(maximum release−spontaneous release)]×100.

(K) FACS-labelling

For FACS-labelling, the CD40L$^+$-Jurkat Clone D1.1 ($5 \times 10^5$ cells) was incubated with 2 µg of CD40:COMP in FACS buffer (PBS, 10% fetal calf serum, and 0.02% NaN$_3$). Fas:COMP were used as negative control. Receptor:COMP was detected by 1 µg of 9E10 anti-myc antibody and subsequent treatment with FITC-labelled goat-anti-mouse antibody (1:100). Incubations were carried out for a period of 20 min at 4° C. in 50 µl FACS buffer.

(L) Cell Proliferation Assay

For the assay of B cell proliferation, CD19$^+$-cells from human peripheral blood lymphocytes (PBL) were purified by magnetic beads and the remaining CD19$^−$ cells were once irradiated (3000 rad). $10^5$ purified CD19$^+$ cells were mixed with $10^5$ CD19$^−$ autologous irradiated PBL in 120 µl of medium which contained sCD40 L at a concentration of 100 ng/ml (1.8 nM), M2-antibody at 10 µg/ml plus or minus protein A at a concentration of 1 µg/ml and the indicated concentrations of CD40:Fc or CD40:COMP. Then, the cells were cultivated for 72 hours in 96 well plates, pulsed with [$^3$H] thymidine (1 µCi/well) for 6 hours and harvested. The incubation of [$^3$H] tymidine was checked by liquid scintillation counting.

7.2 Results of the 7$^{th}$ Embodiment

Fusion proteins which consist of extracellular domains of a receptor being fused to the Fc-part of IgG (receptor:Fc) are known in the art as inhibitory agents for the investigation of receptor ligand interactions. In the 7$^{th}$ embodiment, the size of purified Fas:Fc-fusion protein was examined by exclusion chromatography and it was found that a single peak was eluted having the expected retention time. Fas:Fc containing fractions were able to protect A20-cells which were exposed to a lethal dose of soluble FasL (sFasL) against cell death although the degree of protection (up to 50%) was extraordinarily low, when taking into consideration that the estimated ratio of Fas:Fc to FasL in the experiment was about 1000.

A weak protective activity was observed in several of the early fractions of the eluate, which probably contained minor nondetectable amounts of high molecular weight complexes of Fas:Fc. According to the present invention it was recognized that such higher aggregates of the fusion protein can act as potent inhibitors of FasL-induced cell death. Therefore, this high molecular weight fraction of aggregated Fas:Fc was initially raised by adding the immunoglobulin crosslinking agent protein A. As soon as the analysis was carried out under conditions where only about 10% of the injected Fas:Fc were shifted to the early eluting fractions, it was apparent that a high molecular weight Fas:Fc complex is an effective antagonist of the cytotoxicity induced by FasL. Compared to that, it was found that the remaining Fas:Fc fractions still eluted as a dimer and only a partial protection was awarded to the cells in spite of a ten-fold higher concentration. According to the present invention the results of the 7th embodiment show that the formation of higher Fas:Fc aggregates substantially increases the specific protective activity.

Therefore, according to the present invention complexes of fusion proteins were constructed on the basis of these findings, which show a better avidity with respect to FasL and improve the inhibitory characteristics due to an increase in the degree of oligomerisation. Fusion proteins according to the present invention are, e.g. such fusion proteins in which the extracellular domains of receptors of the TNF family, e.g. Fas, TRAIL-R1, TRAIL-R2, TRAILR-3, TNF-R1 or CD40, are fused to the oligomerised domains of either the so-called cartilage oligomeric protein ((COMP); fusion protein designated as: Receptor:COMP) or the so-called cartilage matrix protein ((CMP); fusion protein: Receptor:CMP) via a 14 aminoacid-long linker. These matrix proteins and their domains, respectivly, have the native property of forming pentameric and trimeric, respectivly, coiled-coil-structures. The above-mentioned fusion proteins (as well as Receptor: Fc fusion proteins as controls) were expressed in mammalian cells and purified by affinity chromatography on metalchelate columns or on protein A. In the 7th embodiment, the receptors Fas and TRAIL-R2 were also bounded to the C-terminal dimerisation domain of the protein osteoprotegrin of the TNF family (Receptor: δN-OPG).

The receptors which were fused to COMP or CMP oligomerized as was shown by slow migration in the polyacrylamide gel under non-reducing conditions. Fas:COMP and TRAIL-R2:CMP eluted as well-defined peaks having apparent molecular weights of about 400 and 170 kDA, respectivly, by application of the gel permeation chromatography method. The molecular weights correspond to pentameric and trimeric, respectively, structures of the fusion proteins. Therefore, it can be concluded from the experiments of the 7th embodiment that the aggregation characteristics of coiled-coil oligomerisation domains of the above-mentioned matrix proteins is not impeded by the fusion to proteins (or protein domains) of the TNF receptor family.

The fusion protein Fas:COMP showed a lower $K_d$ than Fas:Fc when the fusion proteins were allowed to compete with applied Fas:Fc for the sFasL-binding. In agreement to this result, a dissociation constant of 0,77 nM was measured for the FasL-Fas:COMP interaction, which is about 8- to 9-fold lower than comparative values for Fas:Fc. For the vast majority of the cell lines tested it was shown that the in-hibitory activity of Fas:COMP is about 10- to 20-fold higher than that for the dimeric fusion protein Fas:Fc, whereas the results for Fas:Fc aggregates caused by the cross linking protein A(Fas:Fc/PA) showed values between those for Fas:COMP and Fas:Fc. The protective activity of dimeric Fas:δN-OPG fusion protein was comparable to that of the dimeric Fas:Fc complex. Trimeric Fas:CMP inhibited the sFasL-mediated lysis approximately as effectively as Fas:Fc/PA—thus, as a result 5-fold less effective than Fas: COMP. The inhibitory activity of Fas:COMP was good or better than that of FasL-blocking monoclonal antibodies Nok-1, 4H9 and 4A5. In comparison to the Fas:Fc complex, the superior inhibitory activity of Fas:COMP was also evident from experiments with primary murine hepatocytes or from a model system for the activation-induced cell death with anti-CD3-activated Jurkat cells. In all of these experiments a medium protection level resulted for Fas:Fc-PA. Furthermore, it was examined whether Fas:COMP is capable of inhibiting the effect of FasL expressed on CTLs. The death of A20-cells in a 4 hour test system is solely depended on perforin and the FasL-dependent signal transduction pathways, since CTL which are deficient for perforin as well as for FasL have no effect on these cells. In a corresponding experiment, A20 cells were killed by perforin-deficient CTLs as well as by FasL-defizient CTLs, as expected. Fas:Fc and Fas:COMP specifically caused a certain degree of protection for the cells which were exposed to perforin-deficient CTLs.

In a comparison of the affinities of sCD40L to CD40:Fc, CD40:Fc/PA or CD40:COMP according to the present invention by competitive ELISA, a substantial increase in the affinity (30-fold) was observed for the pentamerised receptor while again a medium effect occurred for CD40: Fc/PA (8-fold). With respect to the question of whether CD40: COMP is also able to recognise membrane-bound CD40L, the Jurkat-derivatised cell line D1.1, which expresses the surface protein CD40L constitutively, was used for the oligomerisation of a FACS labelling analysis with the aid of the CD40 fusion proteins as samples. A significant labelling was observed for CD40:COMP according to the present invention, which indicates that CD40-COMP is in fact capable of binding native unprocessed CD40L. In order to examine the specific activity of CD40 fusion protein in a biological system, it was attempted to inhibit the CD40L-dependent proliferation of human B cells which were co-stimulated with anti-B-cell receptor. Neither CD40:Fc nor CD40:Fc/PA were able to impede the proliferation significantly even in the case where they were administrated in high doses. On the contrary, CD40:COMP according to the present invention was capable of blocking the proliferation already at relative low doses.

Summing up, it can be concluded from the observations of the present embodiment that the inhibition of FasL-induced apoptosis by competitive inhibitors increased depending on the degree of oligomerisation and that the relative activities of the various inhibitors (expressed as the proportion of their respective $IC_{50}$ values) remained relatively constant for the various cell lines. The increased inhibitory activity of Fas:COMP according to the present invention in comparison to Fas:Fc is probably the result of its higher avidity. Similar results were also determined for the activity of the CD40 fusion protein according to the present invention. CD40:COMP according to the present invention is distinctly superior to CD40:Fc in vitro with respect to the inhibition of CD40L-induced proliferation of primary B cells. Accordingly, the results of embodiment 7 show that dissociation constants in the low nanomolar region can be obtained for such receptors as, e.g. Fas and CD40, which are natively characterised by a medium affinity for their ligands, if they, as intended by the present invention, are a component of fusion proteins which are characterised by a higher degree of oligomerisation.

We claim:

1. A recombinant fusion protein having at least one component A and at least one component B, wherein component A comprises an extracellular segment of FasL protein capable of binding to the Fas receptor and component B comprises a protein segment of ACRP30 comprising the collagen-like segment of ACRP30 without the globular head domain of ACRP30, which oligomerizes the recombinant fusion protein without the effect of third molecules, and wherein said recombinant fusion protein comprises a linker sequence between component A and component B.

2. A DNA sequence that encodes the fusion protein according to claim 1.

3. An oligomer of the recombinant fusion protein of claim 1.

4. A recombinant fusion protein having at least one component A and at least one component B, wherein component A comprises an extracellular segment of FasL protein capable of binding to the Fas receptor and component B comprises a protein segment of ACRP30 comprising the collagen-like segment of ACRP30 without the globular head domain of ACRP30, which oligomerizes the recombinant fusion protein without the effect of third molecules, wherein component B comprises amino acids 18 to 111 of mACRP30, or amino acids 18 to 108 of hACRP30.

5. An oligomer of the fusion protein of claim 4.

6. A DNA sequence that encodes the fusion protein of claim 4.

7. A recombinant fusion protein having at least one component A and at least one component B, wherein component A comprises an extracellular segment of FasL protein capable of binding to the Fas receptor and component B comprises a protein segment of ACRP30 comprising the collagen-like segment of ACRP30 without the globular head domain of ACRP30, which oligomerizes the recombinant fusion protein without the effect of third molecules, wherein component A is amino acids 139-261 of hFasL.

8. An oligomer of the fusion protein of claim 7.

9. A DNA sequence that encodes the fusion protein of claim 7.

10. A recombinant fusion protein having at least one component A and a least one component B, wherein component A comprises amino acids 139-261 of hFasL and component B comprises amino acids 18-111 of mACRP30 or amino acids 18 to 108 of hACRP30.

11. An oligomer of the fusion protein of claim 10.

12. A DNA sequence that encodes the fusion protein of claim 10.

* * * * *